(12) United States Patent
Guschin et al.

(10) Patent No.: US 9,695,442 B2
(45) Date of Patent: *Jul. 4, 2017

(54) TARGETED DELETION OF CELLULAR DNA SEQUENCES

(71) Applicant: Sangamo BioSciences, Inc., Richmond, CA (US)

(72) Inventors: Dmitry Guschin, Richmond, CA (US); Fyodor Urnov, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/784,634

(22) Filed: Mar. 4, 2013

(65) Prior Publication Data

US 2014/0065667 A1    Mar. 6, 2014

Related U.S. Application Data

(63) Continuation of application No. 11/304,981, filed on Dec. 15, 2005, now Pat. No. 8,409,861, which is a continuation-in-part of application No. 10/912,932, filed on Aug. 6, 2004, now Pat. No. 7,888,121.

(60) Provisional application No. 60/649,515, filed on Feb. 3, 2005, provisional application No. 60/493,931, filed on Aug. 8, 2003, provisional application No. 60/518,253, filed on Nov. 7, 2003, provisional application No. 60/530,541, filed on Dec. 18, 2003, provisional application No. 60/542,780, filed on Feb. 5, 2004, provisional application No. 60/556,831, filed on Mar. 26, 2004, provisional application No. 60/575,919, filed on Jun. 1, 2004.

(51) Int. Cl.
| | |
|---|---|
| *C12N 15/85* | (2006.01) |
| *C07K 14/47* | (2006.01) |
| *C12N 15/10* | (2006.01) |
| *C12N 9/22* | (2006.01) |

(52) U.S. Cl.
CPC .......... *C12N 15/85* (2013.01); *C07K 14/4702* (2013.01); *C12N 9/22* (2013.01); *C12N 15/10* (2013.01); *C07K 2319/81* (2013.01)

(58) Field of Classification Search
CPC ............................ C12N 15/01; C12N 15/1093
See application file for complete search history.

(56) References Cited

U.S. PATENT DOCUMENTS

| | | |
|---|---|---|
| 4,665,184 A | 5/1987 | Dervan et al. |
| 4,942,227 A | 7/1990 | Dervan et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,155 A | 8/1998 | Dervan et al. |
| 5,789,538 A | 8/1998 | Rebar et al. |
| 5,792,640 A | 8/1998 | Chandrasegaran |
| 5,916,794 A | 6/1999 | Chandrasegaran |
| 5,945,577 A | 8/1999 | Stice et al. |
| 5,948,678 A * | 9/1999 | Dujon et al. ................. 435/354 |
| 5,955,341 A | 9/1999 | Kang et al. |
| 6,007,988 A | 12/1999 | Choo et al. |
| 6,013,453 A | 1/2000 | Choo et al. |
| 6,077,710 A | 6/2000 | Susko-Parrish et al. |
| 6,140,081 A | 10/2000 | Barbas |
| 6,140,466 A | 10/2000 | Barbas et al. |
| 6,147,276 A | 11/2000 | Campbell et al. |
| 6,242,568 B1 | 6/2001 | Barbas et al. |
| 6,265,196 B1 | 7/2001 | Chandrasegaran |
| 6,326,166 B1 | 12/2001 | Pomerantz et al. |
| 6,331,658 B1 | 12/2001 | Cooper et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 2002/0022021 A1 | 2/2002 | Emerson |
| 2002/0107214 A1 | 8/2002 | Choulika et al. |
| 2002/0110898 A1 | 8/2002 | Choulika et al. |
| 2002/0152488 A1 | 10/2002 | Cooper et al. |
| 2002/0165356 A1 * | 11/2002 | Barbas, III ............ C07K 14/00 530/350 |
| 2003/0131365 A1 | 7/2003 | Cooper et al. |
| 2003/0232410 A1 | 12/2003 | Liljedahl et al. |

(Continued)

FOREIGN PATENT DOCUMENTS

| | | |
|---|---|---|
| EP | 0 957 165 | 11/1999 |
| WO | WO 95/09233 | 4/1995 |

(Continued)

OTHER PUBLICATIONS

Bai et al. Genetic co-inactivation of macrophage- and T-tropic HIV-1 chemokine coreceptors CCR-5 and CXCR-4 by intrakines. Gene Therapy, vol. 5, pp. 984-994, 1998.*
Petek et al. Frequent endonuclease cleavage at off-target locations in vivo. The American Society of Gene & Cell Therapy, vol. 18, No. 5, pp. 983-986, May 2010.*
Aggarwal, et al., "Novel Site-Specific DNA Endonucleases," *Current Opinion in Structural Biology* 8:19-25 (1998).
Abremski, et al., "Bacteroiphage P1 Site Specific Recombination," *JBC* 259:1509-1514 (1984).
Akopian, et al., "Chimeric Recombinases with Designed DNA Sequence Recognition," *Proc. Nati. Acad. Sci. USA* 100:8688-8691 (2003).
Baubonis, et al., "Genomic Targeting with Purified Cre Recombinase," *Nucleic Acids Res.* 21:2025-2029 (1993).

(Continued)

*Primary Examiner* — Jennifer Dunston
(74) *Attorney, Agent, or Firm* — Pasternak Patent Law; Susan Abrahamson

(57) ABSTRACT

Disclosed herein are methods and compositions for targeted deletion of double-stranded DNA. The compositions include fusion proteins comprising a cleavage domain (or cleavage half-domain) and an engineered zinc finger domain, and polynucleotides encoding same. Methods for targeted deletion include introduction of such fusion proteins, or polynucleotides encoding same, into a cell such that two targeted cleavage events occur. Subsequent cellular repair mechanisms result in deletion of sequences between the two cleavage sites.

10 Claims, 5 Drawing Sheets

(56) References Cited

U.S. PATENT DOCUMENTS

| | | |
|---|---|---|
| 2004/0019002 A1 | 1/2004 | Choulika et al. |
| 2004/0121357 A1 | 6/2004 | Franklin |

FOREIGN PATENT DOCUMENTS

| | | | |
|---|---|---|---|
| WO | 95/17911 A1 | 7/1995 | |
| WO | WO 96/40882 | 12/1996 | |
| WO | WO 97/47758 | 12/1997 | |
| WO | WO 98/53058 | 11/1998 | |
| WO | WO 98/53059 | 11/1998 | |
| WO | WO 98/53060 | 11/1998 | |
| WO | WO 00/09755 | 2/2000 | |
| WO | WO 00/28008 | 5/2000 | |
| WO | WO 00/42219 | 7/2000 | |
| WO | WO 00/46385 | 8/2000 | |
| WO | WO 00/46386 | 8/2000 | |
| WO | WO 00/63365 | 10/2000 | |
| WO | WO 01/05961 | 1/2001 | |
| WO | WO 01/19981 | 3/2001 | |
| WO | WO 01/40798 | 6/2001 | |
| WO | WO 01/66717 | 9/2001 | |
| WO | WO 02/04488 | 1/2002 | |
| WO | WO 03016496 A2 * | 2/2003 | ......... C07K 14/4703 |
| WO | WO 03/080809 | 10/2003 | |
| WO | WO 03/087341 | 10/2003 | |
| WO | WO 2004/037977 A2 | 5/2004 | |

OTHER PUBLICATIONS

Beerli, et al., "Engineering Polydactil Zinc-Finger Transcription Factors," *Nature Biotechnology* 20:135-141 (2000).
Bibikova, el al., "Stimulation of Homologous Recombination through Targeted Cleavage by Chimeric Nucleases." *Molecular and Cellular Biology* 21(1):289-297 (2001).
Bibikova, et al., "Targeted Chromosomal Cleavage and Mutagenisis in *Drosophilia* Using Zinc-Finger Nucleases." *Genetics* 161:1169-1175 (2002).
Bibikova, et al., "Enhancing Gene Targeting with Designed Zinc Finger Nucleases." *Science* 300:764 (2003) Including Supporting Online Materials.
Bitiniate, et al., "FokI Dimerization is Required for DNA Cleavage." *Proc. Natl. Acad. Sci.* 95:10570-10575 (1998).
Brenneman, et al., "Stimulation of Intrachromosomal Homologous Recombination in Human Cells by Electroporation with Site Specific Endonucleases." *Proc. Natl. Acad. Sci.* 93:3608-3612 (1996).
Brisson, et al., "Expression of a Bacterial Gene in Plants by Using a Viral Vector," *Nature* 310:511-514 (1984).
Broglie, et al., "Light Regulated Expression of a Pea Ribulose-1, 5-Biphosphate Carboxylase Small Subunit Gene in Transformed Plant Cells," *Science* 224:838-843 (1984).
Campbell, et al., "Sheep Cloned by Nuclear Transfer from a Cultured Cell Line," *Nature* 380:64-66 (1996).
Cappechi, et al., "Altering the Genome by Homologous Recombination," *Science* 244:1288-1292 (1989).
Chandrasegaran, et al., "Chimeric Restriction Enzymes: What is Next?" *Biol Chem.* 380:841-848 (1999).
Chevalier, et al., "Design, Activity, and Structure of a Highly Specific Artificial Endonuclease." *Molecular Cell* 10:895-905 (2002).
Choulika, et al., "Induction of Homologous Recombination in Mammalian Chromosomes by using the I-SceI System of *Saccharomyces cerevisiae.*" *Molecular and Cellular Biology* 15(4):1968-1973 (1995).
Cohen-Tannoudji, et al., "I-SceI-Induced Gene Replacement at a Natural Locus in Embryonic Stem Cells." *Molecular and Cellular Biology* 18(3):1444-1448 (1998).
Corruzzi, et al., Tissue Specific and Light-Regulated Expression of a Pea Nuclear Gene Encoding the Small Subunit of Ribulose-1, 5-Biphosphate Carboxylase, *Embo. J.* 3:1671-1679 (1984).

Desjarlais, et al., "Use of a Zinc-Finger Consensus Sequence Framework and Specificity Rules to Design Specific DNA Binding Proteins," *Proc. Natl. Acad. Sci. USA* 90:2256-2260 (1993).
Desjarlais, et al., "Towards Rules Relating Zinc Finger Protein Sequences and DNA Binding Site Preferences." *Proc. Natl. Acad. Sci. USA* 89:7345-7349 (1992).
Donoho, et al., "Analysis of Gene targeting and Intrachromosomal Homologous Recombination Stimulated by Genomic Double-Strand Breaks in Mouse Embryonic Stem Cells." *Molecular and Cellular Biology* 18(7):4070-7078 (1998).
Dreier, et al., "Development of Zinc Finger Domains for Recognition of the 5'-Ann-3' Family of DNA Sequences and Their Use in the Construction of Artificial Transcription Factors." *JBC* 276(31):2466-29478 (2001).
Elliot, et al., "Gene Conversion Tracts from Double Strand Break Repair in Mammalian Cells." *Molecular and Cellular Biology* 18(1):93-101 (1998).
Elrod-Erickson, et al., "Binding Studies with Mutants of Zif268." *J. Biol. Chem.* 274(27):19281-19285 (1999).
Evans, et al., Establishment in Culture of Pluripotential Cells from Mouse Embryos, *Nature* 292:154-156 (1981).
Furguson-Smith, "Imprinting and the Epigenetic Asymmetry Between Parental Genomes," *Science* 293:1086-1089 (2001).
Gorlich, et al., "Nucleocytoplasmic Transport." *Science* 271:1513-1518 (1996).
Greisman, et al., "A General Strategy for Selecting High-Affinity Zinc Finger Proteins for Diverse DNA Target Sites." *Science* 275:657-661 (1997).
Gowda, et al., "Identification of Promoter Sequences for the Major RNA Transcripts of Figwort Mosaic and Peanut Chloritic Streak Viruss (Caulimovirus Group)," *J. Cell. Biochem.* 13D:301 (1989).
Gu, et al., "Independent Control of Immunogobulin Switch Recombination at Individual Switch Regions Evidenced through Cre-IoxP-Mediated Gene Targeting," *Cell* 73:1155-1164 (1993).
Gu, et al., "Deletion of a DNA Polymerase B Gene Segment in T Cells Using Cell Type-Specific Gene Targeting," *Science* 265:103-106 (1994).
Gurley, et al., "Upstream Sequences Required for Efficient Expression of a Soybean Heat Shock Gene," *Mol. Cell. Biol.* 6:559-565 (1986).
Hanson, et al., "Analysis of Biological Selections for High-Efficiency Gene Targeting," *Mol. Cell. Biol.* 15:45-51 (1995).
Hicks, et al., "Three Classes of Nuclear Import Signals Bind to Plant Nuclei." *Plant Physiol.* 107:1055-1058 (1995).
Huang, et al., "Splase: A New Class IIS Zinc-Finger Restriction Endonuclease with Specificity for Sp1 Binding Sites." *Journal of Protein Chemistry* 15(5):481-489 (1996).
Jallepalli, et al., "Securin is Required for Chromosomal Stability in Human Cells," *Cell* 105:445-457 (2001).
Jaenisch, "Transgenic Animals," *Science* 240:1468-1474 (1988).
Jasin, et al., "Gene Targeting at the Human CD4 Locus by Epitope Addition," *Genes & Development* 4:157-166 (1990).
Jasin, "Genetic Manipulation of Genomes with Rare-Cutting Endonucleases," *Trends Genet.* 12:224-228 (1996).
Jeggo et al., "Identification of Genes Involved in Repair of Dna Double-Strand Breaks in Mammalian Cells," *Radiation Research* 150:S80-S91 (1998).
Johnson, et al., "Double-Strand-Break-Induced Homologous Recombination in Mammalian Cells." *Biochemical Society Transactions* 29:196-201 (2001).
Khanna, et al., "DNA Double-Strand Breaks: Signaling, Repair and the Cancer Connection." *Nature Genetics* 27:247-254 (2001).
Kim et al., "Construction of a Z-Dna-Specific Restriction Endonuclease," *Proc. Natl. Acad. Sci. USA* 94:12875-12879 (1997).
Kim, et al., "Hybrid Restriction Enzymes: Zinc Finger Fusions of FokI Cleavage Domain." *Proc. Natl. Acad. Sci. USA* 93:1156-1160 (1996).
Kim, et al., "Chimeric Restriction Endonuclease." *Proc. Natl. Acad. Sci. USA* 91:883-887 (1994).
Kim, et al., "Chimeric Restriction Enzyme: Gal4 Fusion to Fold Cleavage Domain." *Biol. Chem.* 379:489-495 (1998).

(56) References Cited

OTHER PUBLICATIONS

Kim, et al., "Insertion and Deletion of Mutants of FokI Restriction Endonuclease." *Journal of Biol. Chem.* 269(50):31978-31982 (1994).
Klien, et al., "Transformation of Microbes, Plants and Animals by Particle Bombardment," *Bio/Techniques* 10:286-291 (1992).
Klien, et al.,"High-Velocity Microprojectiles for Delivering Nucleic Acids into Living Cells," *Nature* 327:70-73 (1987).
Kuehn, et al., "A Potential Animal Model for Lesch-Nyhan Syndrome Through Introduction of HPRT Mutations into Mice," *Nature* 326:295-298 (1987).
Lai, et al., Production of a-1,3-Galctosyltransferase Knockout Pigs by Nuclear Transfer Cloning, *Science* 295:1089-1092 (2002).
Li, et al., "Alteration of the Cleavage Distance of FokI Restriction Endonuclease by Insertion Mutagenesis." *Proc. Natl. Acad. Sci. USA* 90:2764-2768 (1993).
Li, et al., "Functional Domains in FokI Restriction Endonuclease." *Proc. Natl. Acad. Sci. USA* 89:4275-4279 (1992).
Liu, et al., "Validated Zinc Finger Protein Designs for All 16 GNN DNA Triplet Targets." *J. Biol. Chem.* 277(6):3850-3856 (2002).
Mattaj, et al., "Nucleocytoplasmic Transport: The Soluble Phase." *Annu. Rev. Biochem.* 67:265-306 (1998).
McCreath, et al., "Production of Gene-Targeted Sheep by Nuclear Transfer from Cultured Somatic Cells," *Nature* 405:1066-1069 (2000).
Nahon, et al., "Targeting a Truncated Ho-Endonuclaese of Yeast to Novel DNA Sites with Foreign Zinc Fingers." *Nucleic Acids Research* 26(5):1233-1239 (1998).
Odell, et al., "Identification of DNA Sequences Required for Activity of the Cauliflower Mosaic Virus 35S Promoter," *Nature* 313:810-812 (1985).
Pabo, et al., "Design and Selection of Novel Cys2his2 Zinc Finger Proteins," *Annu. Rev. Biochem.* 70:313-340 (2001).
Porteus, et al., "Efficient Gene Targeting Mediated by Adeno-Associated Virus and DNA Double-Strand Breaks," *Mol. Cell. Biol.* 23:3558-3565 (2003).
Porteus, et al., "Chimeric Nucleases Stimulate Gene Targeting in Human Cells." *Science* 300:763 (2003) Including Supporting Online Materials.
Puchta et al., "Homologous Recombination in Plant Cells is Enhanced by In Vivo Induction of Double Strand Breaks into DNA by a Site-Specific Endonuclease," *Nucleic Acids Res.* 21:5034-5040 (1993).
Rebar, et al., "Zinc Finger Phage: Affinity Selection of Fingers with New DNA-Binding Specefcities." *Science* 263:671-673 (1994).
Rebar, et al., "Induction of Angiogenesis in a Mouse Model Using Engineered Transcription Factors," *Nat Med* 8(12): 1427-1432 (2002).
Ridout III, et al., "Nuclear Cloning and Epigenetic Reprogramming of the Genome," *Science* 293:1093-1098 (2001).
Rouet, et al., "Expression of a Site-Specific Endonuclease Stimulates Homologous Recombination in Mammalian Cells." *Proc. Natl. Acad. Sci. USA* 91:6064-6068 (1994).
Rouet, et al., "Introduction of Double-Strand Breaks into the Genome of Mouse Cells by Expression of a Rare-Cutting Endonuclease." *Molecular and Cellular Biology* 14(12):8096-8106 (1994).
Sanford, et al., "An Improved, Helium-Driven Biolistic Device," *Tech.-A J. of Meth. In Cell and Mol. Biol.* 3:3-16 (1991.
Sargent, et al., "Repair of Site-Specific Double-Strand Breaks in a Mammalian Chromosome by Homologous and Illegitimate Recombination." *Molecular and Cellular Biology* 17(1):267-277 (1997).
Schnieke, et al., "Human Factor IX Transgenic Sheep Produced by Transfer of Nuclei from Transfected Fetal Fibroblasts," *Science* 278:2130-2133 (1997).
Sedivy, et al., "Positive Genetic Selection for Gene Disruption in Mammalian Cells by Homologous Recombination," *Proc. Natl. Acad. Sci. USA* 86:227-231 (1989).

Segal. et al., "Endonuclease-Induced, Targeted Homologous Extrachromosomal Recombination in *Xenopus* Oocytes." *Proc. Natl. Acad. Sci. USA* 92:806-810 (1995).
Segal, et al., "Toward Controlling Gene Expression at Will: Selection and Design of Zinc Finger Domains Recognizing Each of the 5'-GNN-3' DNA Target Sequences." *Proc. Natl. Acad. Sci. USA* 96:2758-2763 (1999).
Segal, D. J., "The Use of Zinc Finger Peptides to Study the Role of the Specific factor Binding Sites in the Chromatin Environment." *Methods* 26:76-83 (2002).
Sera, et al., "Rational Design of Artificial Zinc-Finger Proteins Using a Nondegenerate Recognition Code table." *Biochemistry* 41:7074-7081 (2002).
Severin, et al., "Heat-Inducible Hygromycin Resistance in Transgenic Tobacco," *Plant Mol. Biol.* 15:827-833 (1990).
Shi, et al., "Specific DNA-RNA Hybrid Binding by Zinc Finger Proteins." *Science* 268:282-284 (1995).
Shin, et al.,"A Cat Cloned by Nuclear Transplantation," *Nature* 415:859 (2002).
Shillito, et al., "Protoplast Isolation and Transformation," *Pint. Mol. Bio.—A Prac. App.,* Shaw, ed., IRL Press, pp. 161-186 (1988).
Smih, et al., "Double Strand Breaks at the target Locus Stimulate Gene targeting in Embryonic Stem Cells." *Nuc. Acids Res.* 23(24):5012-5019 (1995).
Smith, et al., "A Detailed Study of the Substrate Specefcity of a Chimeric Restriction Enzyme." *Nuc. Acids Res.* 27(2):674-681 (1999).
Smith, et al., "Requirements for Double-Strand Cleavage by Chimeric Restriction Enzymes with Zinc Finger DNA Recognition Domains." *Nuc. Acids Res.* 28(17):3361-3369 (2000).
Sternberg, et al., "Bacteriophage P1 Site-Specific Recombination," *J. Mol. Biol.* 150:467-507 (1981).
Taghian, et al., "Chromosomal Double-Strand Breaks Induce Gene Conversion at High Frequency in Mammalian Cells." *Mole. And Cell. Biol.* 17(11):6386-6393 (1997).
Takamatsu, et al., "Expression of Bacterial Chloramphenicol Acetyltransferase Gene in Tobacco Plants Mediated by TMV-RNA," *EMBO J.* 6:307-311 (1987).
Thierry, et al.,"Cleavage of Yeast and Bacteriophage T& Genomes at a Single Site Using the Rare Cutter Endonuclease I-See I," *Nucleic Acids Res.* 19:189-190 (1991).
Velten, et al., "Isolation of a Dual Plant Promoter Fragment from the Ti Plasmid of Agrobacterium Tumefaciens," *EMBO J.* 3:2723-2730 (1984).
Wilmut, et al., "Viable Offspring Derived from Fetal and Adult Mammalian Cells," *Nature* 385:810-813 (1997).
Wah, et al., "Structure of the Multimodular Endonuclease FokI Bound to DNA." *Nature* 388:97-100 (1997).
Wilson, J. H., "Pointing Fingers at the Limiting Step in Gene targeting." *Nature Biotechnology* 21(7):759-760 (2003).
Wolfe, et al., "Beyond the Recognition Code: Structures of Two Cys2His2 Zinc Finger/TATA Box Complexes." *Structure* 9:727-723 (2001).
Wolfe, et al., "DNA Recognition by Cys2His2Zinc Finger Proteins." *Annu. Rev. Biophys. Biomol. Struct.* 3:183-212 (1999).
Xu, et al., "Engineering a Nicking Endonuclease N. Alwl by Domain Swapping," *PNAS* 98(23):12990-12995 (2001).
Yanez, et al., "Therapeutic Gene targeting." *Gene Therapy* 5:149-159 (1998).
Zhou, et al., "Impaired Macrophage Function and Enhanced T Cell-dependent Immune Response in Mice Lacking CCR5, the Mouse Homologue of the Major HIV-1 Coreceptor," The Journal of Immunology 160:418-425 (1998).
Zuffrey, et al., "Woodchuck Hepatitis Virus Posttranscriptional Regulatory Element Enhances Expression of Transgenes Delivered by Retroviral Vectors." *Journal of Virology* 73(4):2886-2892 (1999).
Wah, et al., "Structure of Fok1 Has Implications for DNA Cleavage," Proc. Natl. Acad. Sci. USA (1998).
Koller, et al., "Inactivating the F32-Microglobulin Locus in Mouse Embryonic Stem Cells by Homologous in Recombination (Class I Antigens/ Gene Targeting)" Genetics 86(1):8932-8935 (1989).

(56) References Cited

OTHER PUBLICATIONS

Steuer, et al., "Chimeras of the Homing Endonuclease PI-SCEI and the Homologous Candida Tropicalis Intein: A Study to Explore the Possibility of Exchanging DNA-Binding Modules to Obtain Highly Specific Endonucleases With Altered Specificity," Chembiochem. 5(2):206-213 (2004).

\* cited by examiner

```
146        156        166        176            616        626        636
TGCTGGTCAT CCTCATCCTG ATAAACTGCA AAAGGCTGAA........CCGCTGCTTG TCATGGTCAT CTGCTACTCGG

TGCTGGTCAT CCTCATCCTG AT                                    CAT CTGCTACTCGG
TGCTGGTCAT CCTCATCCTG AT                                    CAT CTGCTACTCGG
TGCTGGTCAT CCTCATCCTG AT                                    CAT CTGCTACTCGG
TGCTGGTCAT CCTCATCCTG AT                                    CAT CTGCTACTCGG
TGCTGGTCAT CCTCATCCTG AT                                    CAT CTGCTACTCGG
TGCTGGTCAT CCTCATCCTG AT                                    CAT CTGCTACTCGG
TGCTGGTCAT CCTCATCCTG AT                               GGTCAT CTGCTACTCGG
TGCTGGTCAT CCTCATC                                  ATGGTCAT CTGCTACTCGG
TGCTGGTCAT CCTCATC                                  ATGGTCAT CTGCTACTCGG
TGCTGGTCAT CCTCATC                                  ATGGTCAT CTGCTACTCGG
TGCTGGTCAT CCTCATC                                     TGCTACTCGG
TGCTGGTCAT CCTCATCCTG ATA                            TGGTCAT CTGCTACTCGG
TGCTGGTCAT CCTCATCCT                                     CAT CTGCTACTCGG
TGCTGGTCAT CCTCATCCT                                     CAT CTGCTACTCGG
TGCTGGTCAT CCTCATCCC                              TGGTCAT CTGCTACTCGG
<-- additional 151 bp deleted + 20 bp inserted          CTGCTACTCGG
<-- more than 210 additional bp deleted      additional 90 bp deleted -->
```

FIGURE 2

FIGURE 3
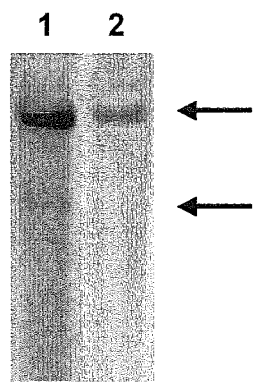

```
      146             156         166         176                 616         626         636
TGCTGGTCAT     CCTCATCCTG ATAAACTGCA AAAGGCTGAA........CCGCTGCTTG TCATGGTCAT CTGCTACTCG

TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG AT                                                 CAT CTGCTACTCG
TGCTGGTCAT     CCTCATCCTG                                              GGTCAT CTGCTACTCG
TGCTGGTCAT     CCTCATCCT                                               GTCAT CTGCTACTCG
TGCTGGTCAT     CCTCATCC                                                GTCAT CTGCTACTCG
TGCTGGTCAT     CCTCATC                                                 GTCAT CTGCTACTCG
TGCTGGTCAT     CCTCATC                                                 CAT CTGCTACTCG
TGCTGGTCAT     CCTCATC                                                  AT CTGCTACTCG
TGCTGGTCAT     CCTCATC                                            TGGTCAT CTGCTACTCG
TGCTGGTCAT     CCTCATC                                           ATGGTCAT CTGCTACTCG
TGCTGGTCAT     CCTCATC                                           ATGGTCAT CTGCTACTCG
TGCTGGTCAT     CCTCATC                                                     TGCTACTCG
```

FIGURE 5

SEQUENCE LISTING

```
<160> NUMBER OF SEQ ID NOS: 84

<210> SEQ ID NO 1
<211> LENGTH: 12
<212> TYPE: PRT
<213> ORGANISM: Artificial Sequence
<220> FEATURE:
<223> OTHER INFORMATION: Amino acid sequence between the zinc finger
      portion and the nuclease half-domain of the ZFP-FokI fusion
      nuclease

<400> SEQUENCE: 1

His Gln Arg Thr His Gln Asn Lys Lys Gln Leu Val
1               5                   10

<210> SEQ ID NO 2
<211> LENGTH: 12
<212> TYPE: DNA
<213> ORGANISM: Homo sapiens

<400> SEQUENCE: 2
gatgaggatg ac                                                          12

<210> SEQ ID NO 3
<211> LENGTH: 7
<212> TYPE: PRT
<213> ORGANISM: Homo sapiens

<400> SEQUENCE: 3

Asp Arg Ser Asn Leu Ser Arg
```

```
1               5

<210> SEQ ID NO 4
<211> LENGTH: 7
<212> TYPE: PRT
<213> ORGANISM: Homo sapiens

<400> SEQUENCE: 4

Thr Ser Ala Asn Leu Ser Arg
1               5

<210> SEQ ID NO 5
<211> LENGTH: 7
<212> TYPE: PRT
<213> ORGANISM: Homo sapiens

<400> SEQUENCE: 5

Arg Ser Asp Asn Leu Ala Arg
1               5

<210> SEQ ID NO 6
<211> LENGTH: 7
<212> TYPE: PRT
<213> ORGANISM: Homo sapiens

<400> SEQUENCE: 6

Val Ser Ser Asn Leu Thr Ser
1               5

<210> SEQ ID NO 7
<211> LENGTH: 12
<212> TYPE: DNA
<213> ORGANISM: Homo sapiens

<400> SEQUENCE: 7
aaactgcaaa ag                                                        12

<210> SEQ ID NO 8
<211> LENGTH: 7
<212> TYPE: PRT
<213> ORGANISM: Homo sapiens

<400> SEQUENCE: 8

Arg Ser Asp His Leu Ser Glu
1               5

<210> SEQ ID NO 9
<211> LENGTH: 7
<212> TYPE: PRT
<213> ORGANISM: Homo sapiens

<400> SEQUENCE: 9

Gln Asn Ala Asn Arg Ile Thr
1               5

<210> SEQ ID NO 10
<211> LENGTH: 7
<212> TYPE: PRT
<213> ORGANISM: Homo sapiens

<400> SEQUENCE: 10

Arg Ser Asp Val Leu Ser Glu
1               5
```

```
<210> SEQ ID NO 11
<211> LENGTH: 7
<212> TYPE: PRT
<213> ORGANISM: Homo sapiens

<400> SEQUENCE: 11

Gln Arg Asn His Arg Thr Thr
1               5

<210> SEQ ID NO 12
<211> LENGTH: 7
<212> TYPE: PRT
<213> ORGANISM: Homo sapiens

<400> SEQUENCE: 12

Arg Ser Asp Asn Leu Ser Val
1               5

<210> SEQ ID NO 13
<211> LENGTH: 7
<212> TYPE: PRT
<213> ORGANISM: Homo sapiens

<400> SEQUENCE: 13

Gln Lys Ile Asn Leu Gln Val
1               5

<210> SEQ ID NO 14
<211> LENGTH: 12
<212> TYPE: DNA
<213> ORGANISM: Homo sapiens

<400> SEQUENCE: 14
gacaagcagc gg                                                           12

<210> SEQ ID NO 15
<211> LENGTH: 7
<212> TYPE: PRT
<213> ORGANISM: Homo sapiens

<400> SEQUENCE: 15

Arg Ser Ala His Leu Ser Glu
1               5

<210> SEQ ID NO 16
<211> LENGTH: 7
<212> TYPE: PRT
<213> ORGANISM: Homo sapiens

<400> SEQUENCE: 16

Arg Ser Ala Asn Leu Ser Glu
1               5

<210> SEQ ID NO 17
<211> LENGTH: 7
<212> TYPE: PRT
<213> ORGANISM: Homo sapiens

<400> SEQUENCE: 17

Arg Ser Ala Asn Leu Ser Val
1               5

<210> SEQ ID NO 18
<211> LENGTH: 7
<212> TYPE: PRT
```

```
<213> ORGANISM: Homo sapiens

<400> SEQUENCE: 18

Asp Arg Ala Asn Leu Ser Arg
1               5

<210> SEQ ID NO 19
<211> LENGTH: 13
<212> TYPE: DNA
<213> ORGANISM: Homo sapiens

<400> SEQUENCE: 19
catctgctac tcg                                                         13

<210> SEQ ID NO 20
<211> LENGTH: 7
<212> TYPE: PRT
<213> ORGANISM: Homo sapiens

<400> SEQUENCE: 20

Arg Ser Asp Ser Leu Ser Lys
1               5

<210> SEQ ID NO 21
<211> LENGTH: 7
<212> TYPE: PRT
<213> ORGANISM: Homo sapiens

<400> SEQUENCE: 21

Asp Asn Ser Asn Arg Ile Lys
1               5

<210> SEQ ID NO 22
<211> LENGTH: 7
<212> TYPE: PRT
<213> ORGANISM: Homo sapiens

<400> SEQUENCE: 22

Arg Ser Ala Val Leu Ser Glu
1               5

<210> SEQ ID NO 23
<211> LENGTH: 7
<212> TYPE: PRT
<213> ORGANISM: Homo sapiens

<400> SEQUENCE: 23

Thr Asn Ser Asn Arg Ile Thr
1               5

<210> SEQ ID NO 24
<211> LENGTH: 14
<212> TYPE: DNA
<213> ORGANISM: Homo sapiens

<400> SEQUENCE: 24
catctgctac tcgg                                                        14

<210> SEQ ID NO 25
<211> LENGTH: 7
<212> TYPE: PRT
<213> ORGANISM: Homo sapiens

<400> SEQUENCE: 25
```

Ala Arg Ser Thr Arg Thr Asn
1               5

<210> SEQ ID NO 26
<211> LENGTH: 21
<212> TYPE: DNA
<213> ORGANISM: Artificial Sequence
<220> FEATURE:
<223> OTHER INFORMATION: PCR primer CCR5longF

<400> SEQUENCE: 26
gatggtgctt tcatgaattc c                                        21

<210> SEQ ID NO 27
<211> LENGTH: 20
<212> TYPE: DNA
<213> ORGANISM: Artificial Sequence
<220> FEATURE:
<223> OTHER INFORMATION: PCR primer CCR5longR

<400> SEQUENCE: 27
gtgtcacaag cccacagata                                          20

<210> SEQ ID NO 28
<211> LENGTH: 12
<212> TYPE: DNA
<213> ORGANISM: Homo sapiens

<400> SEQUENCE: 28
atggctttat gg                                                  12

<210> SEQ ID NO 29
<211> LENGTH: 7
<212> TYPE: PRT
<213> ORGANISM: Homo sapiens

<400> SEQUENCE: 29

Arg Ser Asp His Leu Ser Gln
1               5

<210> SEQ ID NO 30
<211> LENGTH: 7
<212> TYPE: PRT
<213> ORGANISM: Homo sapiens

<400> SEQUENCE: 30

Thr Ser Ser Ala Arg Thr Asn
1               5

<210> SEQ ID NO 31
<211> LENGTH: 7
<212> TYPE: PRT
<213> ORGANISM: Homo sapiens

<400> SEQUENCE: 31

Gln Ser Ser Asp Leu Ser Arg
1               5

<210> SEQ ID NO 32
<211> LENGTH: 7
<212> TYPE: PRT
<213> ORGANISM: Homo sapiens

<400> SEQUENCE: 32

Arg Ser Asp Ala Leu Thr Gln

<210> SEQ ID NO 33
<211> LENGTH: 12
<212> TYPE: DNA
<213> ORGANISM: Homo sapiens

<400> SEQUENCE: 33
gccttggatt tc                                                        12

<210> SEQ ID NO 34
<211> LENGTH: 7
<212> TYPE: PRT
<213> ORGANISM: Homo sapiens

<400> SEQUENCE: 34

Thr Asn Leu Pro Leu Asn Asn
1               5

<210> SEQ ID NO 35
<211> LENGTH: 7
<212> TYPE: PRT
<213> ORGANISM: Homo sapiens

<400> SEQUENCE: 35

Thr Ser Ser Asn Leu Ser Arg
1               5

<210> SEQ ID NO 36
<211> LENGTH: 7
<212> TYPE: PRT
<213> ORGANISM: Homo sapiens

<400> SEQUENCE: 36

Arg Ser Asp Ser Leu Ser Ala
1               5

<210> SEQ ID NO 37
<211> LENGTH: 7
<212> TYPE: PRT
<213> ORGANISM: Homo sapiens

<400> SEQUENCE: 37

Asp Arg Ser Asp Leu Ser Arg
1               5

<210> SEQ ID NO 38
<211> LENGTH: 13
<212> TYPE: DNA
<213> ORGANISM: Homo sapiens

<400> SEQUENCE: 38
acccggacct cag                                                       13

<210> SEQ ID NO 39
<211> LENGTH: 7
<212> TYPE: PRT
<213> ORGANISM: Homo sapiens

<400> SEQUENCE: 39

Thr Ser Ser Thr Arg Lys Thr
1               5

<210> SEQ ID NO 40

```
<211> LENGTH: 7
<212> TYPE: PRT
<213> ORGANISM: Homo sapiens

<400> SEQUENCE: 40

Thr Ser Ser Asp Arg Thr Lys
1               5

<210> SEQ ID NO 41
<211> LENGTH: 13
<212> TYPE: DNA
<213> ORGANISM: Homo sapiens

<400> SEQUENCE: 41
gcttcggcag gct                                                          13

<210> SEQ ID NO 42
<211> LENGTH: 7
<212> TYPE: PRT
<213> ORGANISM: Homo sapiens

<400> SEQUENCE: 42

Arg Ser Asp Asn Leu Arg Glu
1               5

<210> SEQ ID NO 43
<211> LENGTH: 7
<212> TYPE: PRT
<213> ORGANISM: Homo sapiens

<400> SEQUENCE: 43

Arg Ser Asp Asp Leu Ser Lys
1               5

<210> SEQ ID NO 44
<211> LENGTH: 7
<212> TYPE: PRT
<213> ORGANISM: Homo sapiens

<400> SEQUENCE: 44

Gln Ser Ser Asp Leu Arg Arg
1               5

<210> SEQ ID NO 45
<211> LENGTH: 40
<212> TYPE: DNA
<213> ORGANISM: Homo sapiens

<400> SEQUENCE: 45
tgctggtcat cctcatcctg ataaactgca aaaggctgaa                             40

<210> SEQ ID NO 46
<211> LENGTH: 31
<212> TYPE: DNA
<213> ORGANISM: Homo sapiens

<400> SEQUENCE: 46
ccgctgcttg tcatggtcat ctgctactcg g                                      31

<210> SEQ ID NO 47
<211> LENGTH: 36
<212> TYPE: DNA
<213> ORGANISM: Homo sapiens

<400> SEQUENCE: 47
```

```
tgctggtcat cctcatcctg atcatctgct actcgg                                36
```

<210> SEQ ID NO 48
<211> LENGTH: 36
<212> TYPE: DNA
<213> ORGANISM: Homo sapiens

<400> SEQUENCE: 48

```
tgctggtcat cctcatcctg atcatctgct actcgg                                36
```

<210> SEQ ID NO 49
<211> LENGTH: 36
<212> TYPE: DNA
<213> ORGANISM: Homo sapiens

<400> SEQUENCE: 49

```
tgctggtcat cctcatcctg atcatctgct actcgg                                36
```

<210> SEQ ID NO 50
<211> LENGTH: 36
<212> TYPE: DNA
<213> ORGANISM: Homo sapiens

<400> SEQUENCE: 50

```
tgctggtcat cctcatcctg atcatctgct actcgg                                36
```

<210> SEQ ID NO 51
<211> LENGTH: 36
<212> TYPE: DNA
<213> ORGANISM: Homo sapiens

<400> SEQUENCE: 51

```
tgctggtcat cctcatcctg atcatctgct actcgg                                36
```

<210> SEQ ID NO 52
<211> LENGTH: 36
<212> TYPE: DNA
<213> ORGANISM: Homo sapiens

<400> SEQUENCE: 52

```
tgctggtcat cctcatcctg atcatctgct actcgg                                36
```

<210> SEQ ID NO 53
<211> LENGTH: 39
<212> TYPE: DNA
<213> ORGANISM: Homo sapiens

<400> SEQUENCE: 53

```
tgctggtcat cctcatcctg atggtcatct gctactcgg                             39
```

<210> SEQ ID NO 54
<211> LENGTH: 36
<212> TYPE: DNA
<213> ORGANISM: Homo sapiens

<400> SEQUENCE: 54

```
tgctggtcat cctcatcatg gtcatctgct actcgg                                36
```

<210> SEQ ID NO 55
<211> LENGTH: 36
<212> TYPE: DNA
<213> ORGANISM: Homo sapiens

```
<400> SEQUENCE: 55
tgctggtcat cctcatcatg gtcatctgct actcgg                                  36

<210> SEQ ID NO 56
<211> LENGTH: 36
<212> TYPE: DNA
<213> ORGANISM: Homo sapiens

<400> SEQUENCE: 56
tgctggtcat cctcatcatg gtcatctgct actcgg                                  36

<210> SEQ ID NO 57
<211> LENGTH: 27
<212> TYPE: DNA
<213> ORGANISM: Homo sapiens

<400> SEQUENCE: 57
tgctggtcat cctcatctgc tactcgg                                            27

<210> SEQ ID NO 58
<211> LENGTH: 41
<212> TYPE: DNA
<213> ORGANISM: Homo sapiens

<400> SEQUENCE: 58
tgctggtcat cctcatcctg atatggtcat ctgctactcg g                            41

<210> SEQ ID NO 59
<211> LENGTH: 33
<212> TYPE: DNA
<213> ORGANISM: Homo sapiens

<400> SEQUENCE: 59
tgctggtcat cctcatcctc atctgctact cgg                                     33

<210> SEQ ID NO 60
<211> LENGTH: 33
<212> TYPE: DNA
<213> ORGANISM: Homo sapiens

<400> SEQUENCE: 60
tgctggtcat cctcatcctc atctgctact cgg                                     33

<210> SEQ ID NO 61
<211> LENGTH: 37
<212> TYPE: DNA
<213> ORGANISM: Homo sapiens

<400> SEQUENCE: 61
tgctggtcat cctcatccct ggtcatctgc tactcgg                                 37

<210> SEQ ID NO 62
<211> LENGTH: 11
<212> TYPE: DNA
<213> ORGANISM: Homo sapiens

<400> SEQUENCE: 62
ctgctactcg g                                                             11

<210> SEQ ID NO 63
<211> LENGTH: 40
<212> TYPE: DNA
<213> ORGANISM: Homo sapiens
```

```
<400> SEQUENCE: 63
tgctggtcat cctcatcctg ataaactgca aaaggctgaa                          40

<210> SEQ ID NO 64
<211> LENGTH: 30
<212> TYPE: DNA
<213> ORGANISM: Homo sapiens

<400> SEQUENCE: 64
ccgctgcttg tcatggtcat ctgctactcg                                     30

<210> SEQ ID NO 65
<211> LENGTH: 35
<212> TYPE: DNA
<213> ORGANISM: Homo sapiens

<400> SEQUENCE: 65
tgctggtcat cctcatcctg atcatctgct actcg                               35

<210> SEQ ID NO 66
<211> LENGTH: 35
<212> TYPE: DNA
<213> ORGANISM: Homo sapiens

<400> SEQUENCE: 66
tgctggtcat cctcatcctg atcatctgct actcg                               35

<210> SEQ ID NO 67
<211> LENGTH: 35
<212> TYPE: DNA
<213> ORGANISM: Homo sapiens

<400> SEQUENCE: 67
tgctggtcat cctcatcctg atcatctgct actcg                               35

<210> SEQ ID NO 68
<211> LENGTH: 35
<212> TYPE: DNA
<213> ORGANISM: Homo sapiens

<400> SEQUENCE: 68
tgctggtcat cctcatcctg atcatctgct actcg                               35

<210> SEQ ID NO 69
<211> LENGTH: 35
<212> TYPE: DNA
<213> ORGANISM: Homo sapiens

<400> SEQUENCE: 69
tgctggtcat cctcatcctg atcatctgct actcg                               35

<210> SEQ ID NO 70
<211> LENGTH: 35
<212> TYPE: DNA
<213> ORGANISM: Homo sapiens

<400> SEQUENCE: 70
tgctggtcat cctcatcctg atcatctgct actcg                               35

<210> SEQ ID NO 71
<211> LENGTH: 35
<212> TYPE: DNA
```

<213> ORGANISM: Homo sapiens

<400> SEQUENCE: 71
tgctggtcat cctcatcctg atcatctgct actcg    35

<210> SEQ ID NO 72
<211> LENGTH: 35
<212> TYPE: DNA
<213> ORGANISM: Homo sapiens

<400> SEQUENCE: 72
tgctggtcat cctcatcctg atcatctgct actcg    35

<210> SEQ ID NO 73
<211> LENGTH: 35
<212> TYPE: DNA
<213> ORGANISM: Homo sapiens

<400> SEQUENCE: 73
tgctggtcat cctcatcctg atcatctgct actcg    35

<210> SEQ ID NO 74
<211> LENGTH: 35
<212> TYPE: DNA
<213> ORGANISM: Homo sapiens

<400> SEQUENCE: 74
tgctggtcat cctcatcctg atcatctgct actcg    35

<210> SEQ ID NO 75
<211> LENGTH: 35
<212> TYPE: DNA
<213> ORGANISM: Homo sapiens

<400> SEQUENCE: 75
tgctggtcat cctcatcctg atcatctgct actcg    35

<210> SEQ ID NO 76
<211> LENGTH: 38
<212> TYPE: DNA
<213> ORGANISM: Homo sapiens

<400> SEQUENCE: 76
tgctggtcat cctcatcctg atggtcatct gctactcg    38

<210> SEQ ID NO 77
<211> LENGTH: 35
<212> TYPE: DNA
<213> ORGANISM: Homo sapiens

<400> SEQUENCE: 77
tgctggtcat cctcatcctg gtcatctgct actcg    35

<210> SEQ ID NO 78
<211> LENGTH: 35
<212> TYPE: DNA
<213> ORGANISM: Homo sapiens

<400> SEQUENCE: 78
tgctggtcat cctcatcctg gtcatctgct actcg    35

<210> SEQ ID NO 79
<211> LENGTH: 32

```
<212> TYPE: DNA
<213> ORGANISM: Homo sapiens

<400> SEQUENCE: 79
tgctggtcat cctcatcctc atctgctact cg                                    32

<210> SEQ ID NO 80
<211> LENGTH: 30
<212> TYPE: DNA
<213> ORGANISM: Homo sapiens

<400> SEQUENCE: 80
tgctggtcat cctcatccat ctgctactcg                                       30

<210> SEQ ID NO 81
<211> LENGTH: 34
<212> TYPE: DNA
<213> ORGANISM: Homo sapiens

<400> SEQUENCE: 81
tgctggtcat cctcatctgg tcatctgcta ctcg                                  34

<210> SEQ ID NO 82
<211> LENGTH: 35
<212> TYPE: DNA
<213> ORGANISM: Homo sapiens

<400> SEQUENCE: 82
tgctggtcat cctcatcatg gtcatctgct actcg                                 35

<210> SEQ ID NO 83
<211> LENGTH: 35
<212> TYPE: DNA
<213> ORGANISM: Homo sapiens

<400> SEQUENCE: 83
tgctggtcat cctcatcatg gtcatctgct actcg                                 35

<210> SEQ ID NO 84
<211> LENGTH: 26
<212> TYPE: DNA
<213> ORGANISM: Homo sapiens

<400> SEQUENCE: 84
tgctggtcat cctcatctgc tactcg                                           26
```

TARGETED DELETION OF CELLULAR DNA SEQUENCES

CROSS-REFERENCE TO RELATED APPLICATIONS

This application is a continuation is a continuation of U.S. patent application Ser. No. 11/304,981, filed Dec. 15, 2005, now U.S. Pat. No. 8,409,861, which is continuation-in-part of U.S. patent application Ser. No. 10/912,932, filed Aug. 6, 2004, now U.S. Pat. No. 7,888,121, and which claims the benefit of U.S. Provisional Application No. 60/649,515, filed Feb. 3, 2005. Application Ser. No. 10/912,932 also claims the benefit of the following U.S. provisional patent applications: 60/493,931 filed Aug. 8, 2003; 60/518,253 filed Nov. 7, 2003; 60/530,541 filed Dec. 18, 2003; 60/542,780 filed Feb. 5, 2004; 60/556,831 filed Mar. 26, 2004 and 60/575,919 filed Jun. 1, 2004. The disclosures of all of the above are hereby incorporated by reference in their entireties for all purposes

STATEMENT OF RIGHTS TO INVENTIONS MADE UNDER FEDERALLY SPONSORED RESEARCH

Not applicable.

TECHNICAL FIELD

The present disclosure is in the field of genome engineering and targeted deletion (i.e. "knock-out" technology).

BACKGROUND

A major area of interest in genome biology, especially in light of the determination of the complete nucleotide sequences of a number of genomes, is the targeted alteration of genome sequences. One such alteration is deletion, i.e., removal of sequences from a genome. Deletions can be as small as a single nucleotide pair, or can encompass hundreds, thousands or even millions of nucleotide pairs. The ability to reproducibly induce targeted deletions is useful in the identification of gene function (e.g., by gene "knock-out" studies) and can also be useful for inactivating genes (e.g., viral receptors) whose function is required for pathological processes.

Induction of small deletions by targeted cleavage of chromosomal DNA using zinc finger/nuclease fusion proteins (ZFNs) has been described. See, for example, WO 03/87341 and U.S. Patent Application Publication No. 2005/0064474. In brief, when a ZFN dimer (or any site-specific nuclease) is expressed within a cell, the process of targeted cleavage, followed by error-prone repair, can lead to generation of deletions, most of which are of fewer than about 20 bases, at or near the site of nuclease cleavage.

The process of ZFN-mediated mutagenesis as currently implemented using a single ZFN dimer has a number of limitations. First, the sizes of the deletions introduced by this method are generally quite small. Although deletions in excess of 100 bp are occasionally seen, the vast majority of deletions (probably more than 90%) are of fewer than about 20 bp. Therefore the method is unsuitable for generating large deletions at high efficiency. The ability to generate large deletions at high frequency would be required if, for example, it were necessary to eliminate entire regulatory region of a gene.

A second shortcoming of existing methods for ZFN-mediated mutagenesis is that the heterogeneity of the deletions, coupled with their small sizes, makes it extremely difficult to monitor or quantify the mutagenesis process using conventional approaches such as PCR. By contrast, larger deletions are much more readily detected and quantified in a background of excess unmodified gene sequence using a standard method such as PCR followed by agarose gel electrophoresis.

Thus, methods for reproducibly obtaining large deletions of chromosomal sequence at high frequency would be useful in a number of areas of genome biology.

SUMMARY

The present disclosure provides compositions and methods for targeted mutagenesis, particularly deletion mutagenesis, of double-stranded DNA sequences. Thus, in one embodiment, a method for deleting sequences in a region of interest in double-stranded DNA is provided, the method comprising expressing first, second, third and fourth fusion proteins in a cell, wherein each of the fusion proteins comprises (i) a zinc finger DNA-binding domain that binds to a target site in the DNA, and (ii) a cleavage half-domain; further wherein (a) the first and second fusion proteins bind to first and second target sites respectively, wherein a first cleavage site lies between the first and second target sites (i.e., the first and second target sites straddle the first cleavage site) and (b) the third and fourth fusion proteins bind to third and fourth target sites respectively, wherein a second cleavage site lies between the third and fourth target sites (i.e., the third and fourth target sites straddle the second cleavage site); such that the first and second fusion proteins cleave the DNA at the first cleavage site, the third and fourth fusion proteins cleave the DNA at the second cleavage site, and DNA ends are rejoined such that sequences between the first and second cleavage sites are deleted.

Also provided is a method for deleting sequences in a region of interest in double-stranded DNA, the method comprising expressing first and second nucleases in a cell, wherein the first nuclease cleaves a first cleavage site and the second nuclease cleaves a second cleavage site; and DNA ends are rejoined such that sequences between the first and second cleavage sites are deleted.

In certain embodiments, at least one of the nucleases is a fusion protein comprising (i) a zinc finger DNA-binding domain that binds to a target site in the DNA, wherein the target site is at or adjacent to the first or second cleavage site; and (ii) a cleavage domain.

Four DNA ends are generated by cleavage at the two cleavage sites. First and second DNA ends are generated by cleavage at the first cleavage site; while third and fourth DNA ends are generated by cleavage at the second cleavage site. In certain embodiments, the first and second cleavage sites are present on the same DNA molecule (e.g., on the same chromosome). In these cases, if the second and third ends, as defined above, are considered to be part of a DNA fragment containing sequences that lie between the first and second cleavage sites (i.e. a fragment that is released by cleavage at the first and second cleavage sites), then rejoining of the first and fourth ends results in deletion of sequences between the first and second cleavage sites. An alternative outcome is inversion of some or all of the sequences located between the first and second cleavage sites.

If the first and second cleavage sites are located on different chromosomes, chromosomal translocations and/or chromosomal fusions can result. Finally, targeted cleavages and resultant deletion can also occur on extrachromosomal nucleic acids, such as episomes, intracellular vectors, organellar genomes, etc.

In certain instances, ends generated directly by the cleavage event (e.g., the first and fourth DNA ends) may be rejoined to cause a deletion. In other instances, the ends generated by cleavage may be further processed (e.g., by exonucleolytic resection) and these ends resulting from cleavage can be rejoined. Rejoining can occur by cellular repair mechanisms such as those collectively denoted "non-homologous end joining."

As described above, in certain embodiments, sequences in a region of interest are deleted, wherein the region of interest is in cellular chromatin. In these cases, the first and second cleavage sites can be on the same chromosomes, on different chromosomes, on an extrachromosomal nucleic acid, or the first cleavage sit can be present on a chromosome and the second cleavage site can be present on an extrachromosomal nucleic acid.

The target sites bound by the fusion proteins are present in pairs wherein, for each pair of target sites, a cleavage site lies therebetween. Thus, the first and second target sites straddle a first cleavage site and the third and fourth target sites straddle a second cleavage site. The target sites can be separated by any number of nucleotide pairs, commensurate with dimerization of the fusion proteins to regenerate a functional cleavage domain. As described elsewhere in this disclosure, maximal cleavage efficiency varies with both the distance between target sites and the length of the linker sequences between the zinc finger portion and the nuclease half-domain portion of the fusion proteins. Accordingly, the first and second target sites can be separated by 1, 2, 3, 4, 5, 6, 7, 8, 9, 10 or more nucleotide pairs. Similarly, the third and fourth target sites can be separated by 1, 2, 3, 4, 5, 6, 7, 8, 9, 10 or more nucleotide pairs. When discussing the distance between target sites, this distance is expressed as the number of nucleotide pairs intervening between the near edges of the target sites, and does not include any nucleotide pair that is present in either of the target sites.

The size of a deletion induced by the disclosed methods and compositions is determined by the distance between the first and second cleavage sites. Accordingly, deletions of any size, in any region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein.

The region of interest, in which deletion is induced, can be in a gene. The gene can be a gene involved in a disease or pathological condition. For example, the gene can be a viral receptor. Certain chemokine receptors also function as viral receptors; for example, the chemokine receptor CCR-5 also functions a receptor for human immunodeficiency virus (HIV), the causative agent of acquired immune deficiency syndrome (AIDS). Thus, the present disclosure provides methods for inducing targeted deletions in a CCR-5 gene, optionally a human CCR-5 gene, for treatment of AIDS.

Also provided are deleted CCR-5 gene sequences and cells comprising deleted CCR-5 genes; optionally, human cells. In certain embodiments, the cells are primary cells obtained from an individual, which may optionally be returned to the same individual or a different individual. In certain embodiments, the primary cells are T-cells or dendritic cells.

Cells can also include cultured cells, cells in an organism and cells that have been removed from an organism for treatment in cases where the cells and/or their descendants will be returned to the organism after treatment. A region of interest in cellular chromatin can be, for example, a genomic sequence or portion thereof. Compositions include fusion polypeptides comprising an engineered zinc finger binding domain (e.g., a zinc finger binding domain having a novel specificity) and a cleavage domain, and fusion polypeptides comprising an engineered zinc finger binding domain and a cleavage half-domain. Cleavage domains and cleavage half domains can be obtained, for example, from various restriction endonucleases and/or homing endonucleases.

Cellular chromatin can be present in any type of cell including, but not limited to, prokaryotic and eukaryotic cells, fungal cells, plant cells, animal cells, mammalian cells, primate cells and human cells.

A protein e.g., a fusion protein, can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the protein. Methods for polynucleotide and polypeptide delivery to cells are presented elsewhere in this disclosure.

In the disclosed methods for targeted deletion, the cleavage half-domains can be derived from the same endonuclease or from different endonucleases. Endonucleases include, but are not limited to, homing endonucleases and restriction endonucleases. Exemplary restriction endonucleases are Type IIS restriction endonucleases; an exemplary Type IIS restriction endonuclease is Fok I.

In certain embodiments, a cleavage domain can comprise two cleavage half-domains that are covalently linked in the same polypeptide. The two cleavage half-domains can be derived from the same endonuclease or from different endonucleases. The cleavage half domain can be derived from, for example, a homing endonuclease or a restriction endonuclease, for example, a Type IIS restriction endonuclease. An exemplary Type IIS restriction endonuclease is Fok I.

In certain embodiments, it is possible to obtain increased cleavage specificity by utilizing fusion proteins in which one or both cleavage half-domains contains an alteration in the amino acid sequence of the dimerization interface.

In the aforementioned methods for targeted deletion, the target sites for the fusion proteins can comprise any number of nucleotides. Preferably, they are at least nine nucleotides in length, but they can also be larger (e.g., 10, 11, 12, 13, 14, 15, 16, 17, 18 and up to 100 nucleotides, including any integral value between 9 and 100 nucleotides); moreover, different target sequences need not necessarily be the same length. The distance between the nearest edges of the target sites can be any integral number of nucleotide pairs between 1 and 50, (e.g., 5 or 6 base pairs) as measured from the near end of one binding site to the closest end of the other binding site.

In the aforementioned methods for targeted deletion, cellular chromatin can be cleaved at a site located between the target sites of two fusion proteins. In certain embodiments, the target sites are on opposite DNA strands. Moreover, expression of the fusion proteins in the cell can be accomplished either by introduction of the proteins into the cell or by introduction of one or more polynucleotides into the cell, which are optionally transcribed (if the polynucleotide is DNA), and the transcript(s) translated, to produce the fusion proteins. For example, two polynucleotides, each comprising sequences encoding one pair of fusion proteins, can be introduced into a cell. Alternatively, a single polynucleotide comprising sequences encoding both pairs of fusion proteins can be introduced into the cell.

In any of the methods described herein, a zinc finger binding domain can be engineered, for example designed and/or selected. See, for example, U.S. Pat. Nos. 5,789,538; 6,007,988; 6,013,453; 6,140,466; 6,242,568; 6,410,248; 6,453,242; 6,534,261; 6,733,970; 6,746,838; 6,785,613; 6,790,941; 6,794,136; 6,866,997 and 6,933,113, as well as U.S. Patent Application Publication No. 2005/0064477. See also WO 02/42459.

Polynucleotides encoding fusions between a zinc finger binding domain and a cleavage domain or cleavage half-domain can be DNA or RNA, can be linear or circular, and can be single-stranded or double-stranded. They can be delivered to the cell as naked nucleic acid, as a complex with one or more delivery agents (e.g., liposomes, poloxamers) or contained in a viral delivery vehicle, such as, for example, an adenovirus, adeno-associated virus (AAV) or lentivirus. A polynucleotide can encode one or more fusion proteins.

BRIEF DESCRIPTION OF THE DRAWINGS

FIG. 2 shows nucleotide sequences of amplification products of the CCR-5 gene obtained from K562 cells that had been transfected with two plasmids: one encoding a pair of ZFNs designed to cleave between +162 and +168 of the human CCR-5 gene and the other encoding a pair of ZFNs designed to cleave between +627 and +633 of the human CCR-5 gene (i.e., corresponding to lane 4 of FIG. 1). The topmost line shows a partial nucleotide sequence of the wild-type human CCR-5 gene from +146 to +185 (SEQ ID NO:45) and from +616 to +646 (SEQ ID NO:46), with the ZFN target sites underlined. Coordinates are with respect to the first nucleotide pair of the translation initiation codon.

Each of the remaining lines (SEQ ID NOS:47-62) represents a contiguous nucleotide sequence obtained from an amplification product of DNA obtained from cells that had been transfected as described in the preceding paragraph. In the written representation shown in the Figure, portions of each contiguous sequence have been separated for purposes of alignment with the wild-type sequence. The bottom-most two lines provide descriptions of two additional sequences that were obtained.

FIG. 3 shows an autoradiogram of a Southern blot of genomic DNA purified from transfected K562 cells and digested with XhoI and NdeI. Lane 1 shows DNA from cells transfected with two plasmids: one encoding a pair of ZFNs designed to cleave between +162 and +168 of the human CCR-5 gene and the other encoding a pair of ZFNs designed to cleave between +627 and +633 of the human CCR-5 gene. Lane 2 shows DNA from cells transfected with a plasmid encoding GFP. The upper arrow indicates a band derived from amplification of wild-type sequences; the lower arrow identifies a band obtained from amplification of deleted CCR-5 loci.

A schematic diagram of a portion of the human CCR-5 gene, indicating relevant restriction enzyme recognition sites, ZFN target sites and the approximate map position of the fragment used as probe, is shown below the autoradiogram. Numbering is with respect to the first nucleotide pair of the initiation codon.

Figure 4:
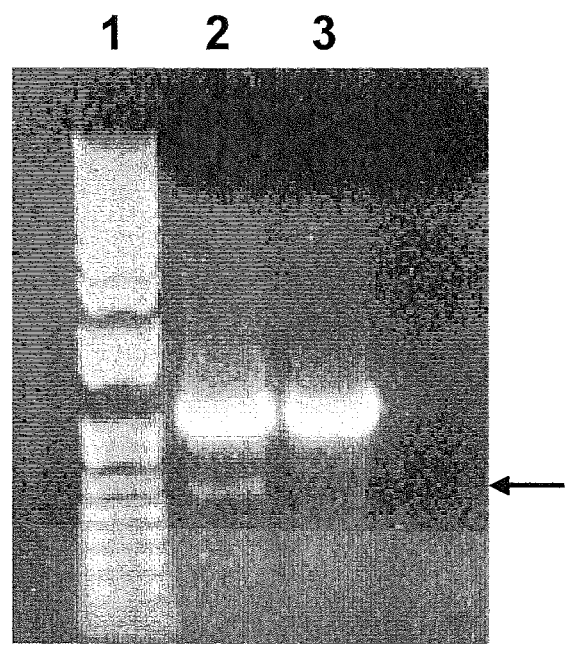

FIG. 4 is a photograph of an agarose gel in which amplification products of the human CCR-5 gene were analyzed. Lane 1 shows size markers. Lane 2 shows amplification products of DNA from human T-cells transfected with a plasmid encoding a pair of ZFNs designed to cleave between +162 and +168 of the human CCR-5 gene and a plasmid encoding a pair of ZFNs designed to cleave between +627 and +633 of the human CCR-5 gene. Lane 3 shows amplification products of DNA from human T-cells transfected with a plasmid encoding green fluorescent protein. The arrow indicates a band representing amplification products of deleted CCR-5 loci.

FIG. 5 shows nucleotide sequences of amplification products of the CCR-5 gene obtained from primary human T-cells that had been transfected with two plasmids: one encoding a pair of ZFNs designed to cleave between +162 and +168 of the human CCR-5 gene and the other encoding a pair of ZFNs designed to cleave between +627 and +633 of the human CCR-5 gene. The topmost line shows a partial nucleotide sequence of the wild-type human CCR-5 gene from +146 to +185 (SEQ ID NO: 63) and from +616 to +645 (SEQ ID NO: 64). The target sites for the ZFNs are underlined. Coordinates are with respect to the first nucleotide pair of the translation initiation codon.

Each of the remaining lines (SEQ ID NOS:65-84) represents a contiguous nucleotide sequence obtained from an amplification product of DNA obtained from cells that had been transfected as described in the preceding paragraph. In the written representation shown in the Figure, portions of each contiguous sequence have been separated for purposes of alignment with the wild-type sequence.

DETAILED DESCRIPTION

Disclosed herein are compositions and methods useful for targeted deletion of sequences in double-stranded DNA (e.g., cellular chromatin). Double-stranded DNA includes that present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Chromosomal sequences can be normal (i.e., wild-type) or mutant; mutant sequences can comprise, for example, insertions, deletions, translocations, rearrangements, and/or point mutations. A chromosomal sequence can also comprise one of a number of different alleles.

Compositions useful for targeted deletion include pairs of fusion proteins, each fusion protein comprising a cleavage domain (or a cleavage half-domain) and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any sequence. Thus, by identifying a target genomic region, the deletion of which is desired, one can, according to the methods disclosed herein, construct one or more fusion proteins comprising a cleavage domain (or cleavage half-domain) and a zinc finger domain engineered to recognize a target sequence in said genomic region. The presence of such fusion proteins in a cell results in binding of the fusion proteins to their target sites, cleavage at two cleavage sites, and deletion of sequences therebetween.

Thus, to obtain targeted deletion, cells are treated simultaneously with a pair of ZFN dimers, which stimulates the highly efficient deletion of DNA lying between the sites cleaved by the two dimers. In this context, the term "ZFN dimer" refers to a pair of zinc finger/cleavage half domain fusion proteins, each of which binds to a distinct target site such that DNA is cleaved at a cleavage site which lies between the target sites.

Advantages of the methods for targeted deletion mutagenesis disclosed herein include:

1) The process can be used for highly efficient deletion of large DNA sequences (e.g., several hundred base pairs). This enables disruption of DNA elements (e.g., exons, introns, regulatory sequences) that may not be completely removable via introduction of small (<20 bp) deletions.

2) The process is readily monitored using standard molecular biology methods such as PCR followed by agarose gel electrophoresis, as well as Southern blot analysis.

3) The induction of large deletions occurs at an efficiency that is substantially enhanced relative to the mutational efficiencies achieved by cleavage with either of the individual ZFN dimers used in the process. Thus use of a pair of ZFN dimers provides a general means for achieving deletion efficiencies which are higher than those achievable using a single ZFN dimer.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. Details of these programs can be found online. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic*

*Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotides pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobilityshift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Target Sites

The disclosed methods and compositions include fusion proteins comprising a cleavage domain (or a cleavage half-domain) and a zinc finger domain, in which the zinc finger domain, by binding to a sequence in cellular chromatin (e.g., a target site or a binding site), directs the activity of the cleavage domain (or cleavage half-domain) to the vicinity of the sequence and, hence, induces cleavage in the vicinity of the target sequence. As set forth elsewhere in this disclosure, a zinc finger domain can be engineered to bind to virtually any desired sequence. Accordingly, after identifying a region of interest containing a sequence at which cleavage or recombination is desired, one or more zinc finger binding domains can be engineered to bind to one or more sequences in the region of interest. Expression of a fusion protein comprising a zinc finger binding domain and a cleavage domain (or of two fusion proteins, each comprising a zinc finger binding domain and a cleavage half-domain), in a cell, effects cleavage in the region of interest.

Selection of a sequence in cellular chromatin for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

Zinc Finger Binding Domains

A zinc finger binding domain comprises one or more zinc fingers. Miller et al. (1985) *EMBO J.* 4:1609-1614; Rhodes (1993) *Scientific American* February:56-65; U.S. Pat. No. 6,453,242. Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261.

Exemplary selection methods, including phage display and two-hybrid systems, are disclosed in U.S. Pat. Nos. 5,789,538; 5,925,523; 6,007,988; 6,013,453; 6,410,248;

6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Cleavage Domains

The cleavage domain portion of the fusion proteins disclosed herein can be obtained from any endo- or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain (e.g., fusion proteins comprising a zinc finger binding domain and a cleavage half-domain) can be derived from any nuclease or portion thereof, as set forth above, that requires dimerization for cleavage activity. In general, two fusion proteins are required for cleavage if the fusion proteins comprise cleavage half-domains. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

In general, if two fusion proteins are used, each comprising a cleavage half-domain, the primary contact strand for the zinc finger portion of each fusion protein will be on a different DNA strands and in opposite orientation. That is, for a pair of ZFP/cleavage half-domain fusions, the target sequences are on opposite strands and the two proteins bind in opposite orientation.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

Exemplary Type IIS restriction enzymes are listed in Table 1. Additional restriction enzymes also contain separable binding and cleavage domains, and these are contemplated by the present disclosure. See, for example, Roberts et al. (2003) *Nucleic Acids Res.* 31:418-420.

TABLE 1

Some Type IIS Restriction Enzymes

| | | |
|---|---|---|
| Aar I | BsrB I | SspD5 I |
| Ace III | BsrD I | Sth132 I |
| Aci I | BstF5 I | Sts I |
| Alo I | Btr I | TspDT I |
| Bae I | Bts I | TspGW I |
| Bbr7 I | Cdi I | Tth111 II |
| Bbv I | CjeP I | UbaP I |
| Bbv II | Drd II | Bsa I |
| BbvC I | Eci I | BsmB I |
| Bcc I | Eco31 I | |
| Bce83 I | Eco57 I | |
| BceA I | Eco57M I | |
| Bcef I | Esp3 I | |
| Bcg I | Fau I | |
| BciV I | Fin I | |
| Bfi I | Fok I | |
| Bin I | Gdi II | |
| Bmg I | Gsu I | |
| Bpu10 I | Hga I | |
| BsaX I | Hin4 II | |
| Bsb I | Hph I | |
| BscA I | Ksp632 I | |
| BscG I | Mbo II | |
| BseR I | Mly I | |
| BseY I | Mme I | |
| Bsi I | Mnl I | |
| Bsm I | Pfl1108 I | |
| BsmA I | Ple I | |
| BsmF I | Ppi I | |
| Bsp24 I | Psr I | |
| BspG I | RleA I | |
| BspM I | Sap I | |
| BspNC I | SfaN I | |
| Bsr I | Sim I | |

Zinc Finger Domain-Cleavage Domain Fusions

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In general, the components of the fusion proteins (e.g, ZFP-Fok I fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus.

In the disclosed fusion proteins, the amino acid sequence between the zinc finger binding domain (which is delimited by the N-terminal most of the two conserved cysteine residues and the C-terminal-most of the two conserved histidine residues) and the cleavage domain (or half-domain) is denoted the "ZC linker" The ZC linker is to be distinguished from the inter-finger linkers discussed above. For instance, in a ZFP-Fok I fusion protein (in which the components are arranged: N terminus-zinc finger binding domain-Fok I cleavage half domain-C terminus), the ZC linker is located between the second histidine residue of the C-terminal-most zinc finger and the N-terminal-most amino acid residue of the cleavage half-domain (which is generally glutamine (Q) in the sequence QLV). The ZC linker can be any amino acid sequence. To obtain optimal cleavage, the length of the linker and the distance between the target sites (binding sites) are interrelated. See, for example, Smith et al. (2000) *Nucleic Acids Res.* 28:3361-3369; Bibikova et al. (2001) *Mol. Cell. Biol.* 21:289-297, noting that their notation for linker length differs from that given here. For example, for ZFP-Fok I fusions having a ZC linker length of four amino acids (as defined herein), optimal cleavage occurs when the binding sites for the fusion proteins are located 6 or 16 nucleotides apart (as measured from the near edge of each binding site).

Methods for Targeted Cleavage

The disclosed methods and compositions can be used to cleave DNA at a region of interest in cellular chromatin (e.g., at a desired or predetermined site in a genome, for example, in a gene, either mutant or wild-type). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near which cleavage is desired. The fusion protein, or a polynucleotide encoding same, is introduced into a cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (See, for example, Smith et al. (2000) *Nucleic Acids Res.* 28:3361-3369; Bibikova et al. (2001) *Mol. Cell. Biol.* 21:289-297) and the length of the ZC linker in each fusion protein.

For ZFP-FokI fusion nucleases, the length of the linker between the ZFP and the FokI cleavage half-domain (i.e., the ZC linker) can influence cleavage efficiency. In one experimental system utilizing a ZFP-FokI fusion with a ZC linker of 4 amino acid residues, optimal cleavage was obtained when the near edges of the binding sites for two ZFP-FokI nucleases were separated by 6 base pairs. This particular fusion nuclease comprised the following amino acid sequence between the zinc finger portion and the nuclease half-domain:

(SEQ ID NO: 1)
HQRTHQNKKQLV in which the two conserved histidines in the C-terminal portion of the zinc finger and the first three residues in the FokI cleavage half-domain are underlined. Accordingly, the linker sequence in this construct is QNKK. Bibikova et al. (2001) *Mol. Cell. Biol.* 21:289-297. The present inventors have constructed a number of ZFP-FokI fusion nucleases having a variety of ZC linker lengths and sequences, and analyzed the cleavage efficiencies of these nucleases on a series of substrates having different distances between the ZFP binding sites. See Example 4.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian genome, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins are bound, its cleavage half-domain forms a dimer with the dominant negative mutant half-domain, and undesirable, non-specific cleavage does not occur.

Three catalytic amino acid residues in the Fok I cleavage half-domain have been identified: Asp 450, Asp 467 and Lys 469. Bitinaite et al. (1998) *Proc. Natl. Acad. Sci. USA* 95: 10,570-10,575. Thus, one or more mutations at one of these residues can be used to generate a dominant negative mutation. Further, many of the catalytic amino acid residues of other Type IIS endonucleases are known and/or can be determined, for example, by alignment with Fok I sequences and/or by generation and testing of mutants for catalytic activity.

Dimerization Domain Mutations in the Cleavage Half-Domain

Methods for targeted cleavage which involve the use of fusions between a ZFP and a cleavage half-domain (such as, e.g., a ZFP/FokI fusion) require the use of two such fusion molecules, each generally directed to a distinct target sequence. Target sequences for the two fusion proteins can be chosen so that targeted cleavage is directed to a unique site in a genome, as discussed above. A potential source of reduced cleavage specificity could result from homodimerization of one of the two ZFP/cleavage half-domain fusions. This might occur, for example, due to the presence, in a genome, of inverted repeats of the target sequences for one of the two ZFP/cleavage half-domain fusions, located so as to allow two copies of the same fusion protein to bind with an orientation and spacing that allows formation of a functional dimer.

One approach for reducing the probability of this type of aberrant cleavage at sequences other than the intended target site involves generating variants of the cleavage half-domain that minimize or prevent homodimerization. Preferably, one or more amino acids in the region of the half-domain involved in its dimerization are altered. In the crystal structure of the FokI protein dimer, the structure of the cleavage half-domains is reported to be similar to the arrangement of the cleavage half-domains during cleavage of DNA by FokI. Wah et al. (1998) *Proc. Natl. Acad. Sci. USA* 95:10564-10569. This structure indicates that amino acid residues at positions 483 and 487 play a key role in the dimerization of the FokI cleavage half-domains. The structure also indicates that amino acid residues at positions 446, 447, 479, 483, 484, 486, 487, 490, 491, 496, 498, 499, 500, 531, 534, 537, and 538 are all close enough to the dimerization interface to influence dimerization. Accordingly, amino acid sequence alterations at one or more of the aforementioned positions will likely alter the dimerization properties of the cleavage half-domain. Such changes can be introduced, for example, by constructing a library containing (or encoding) different amino acid residues at these positions and selecting variants with the desired properties, or by rationally designing individual mutants. In addition to preventing homodimerization, it is also possible that some of these mutations may increase the cleavage efficiency above that obtained with two wild-type cleavage half-domains.

Accordingly, alteration of a FokI cleavage half-domain at any amino acid residue which affects dimerization can be used to prevent one of a pair of ZFP/FokI fusions from undergoing homodimerization which can lead to cleavage at undesired sequences. Thus, for targeted cleavage using a pair of ZFP/FokI fusions, one or both of the fusion proteins can comprise one or more amino acid alterations that inhibit self-dimerization, but allow heterodimerization of the two fusion proteins to occur such that cleavage occurs at the desired target site. In certain embodiments, alterations are present in both fusion proteins, and the alterations have additive effects; i.e., homodimerization of either fusion, leading to aberrant cleavage, is minimized or abolished, while heterodimerization of the two fusion proteins is facilitated compared to that obtained with wild-type cleavage half-domains. See Example 5.

Methods for Targeted Alteration of Genomic Sequences and Targeted Recombination

Also described herein are methods of replacing a genomic sequence (e.g., a region of interest in cellular chromatin) with a homologous non-identical sequence (i.e., targeted recombination). Previous attempts to replace particular sequences have involved contacting a cell with a polynucleotide comprising sequences bearing homology to a chromosomal region (i.e., a donor DNA), followed by selection of cells in which the donor DNA molecule had undergone homologous recombination into the genome. The success rate of these methods is low, due to poor efficiency of homologous recombination and a high frequency of non-specific insertion of the donor DNA into regions of the genome other than the target site.

The present disclosure provides methods of targeted sequence alteration characterized by a greater efficiency of targeted recombination and a lower frequency of non-specific insertion events. The methods involve making and using engineered zinc finger binding domains fused to cleavage domains (or cleavage half-domains) to make one or more targeted double-stranded breaks in cellular DNA. Because double-stranded breaks in cellular DNA stimulate homologous recombination several thousand-fold in the vicinity of the cleavage site, such targeted cleavage allows for the alteration or replacement (via homologous recombination) of sequences at virtually any site in the genome.

In addition to the fusion molecules described herein, targeted replacement of a selected genomic sequence also requires the introduction of the replacement (or donor) sequence. The donor sequence can be introduced into the cell prior to, concurrently with, or subsequent to, expression of the fusion protein(s). The donor polynucleotide contains sufficient homology to a genomic sequence to support homologous recombination between it and the genomic sequence to which it bears homology. Approximately 25, 50 100 or 200 nucleotides or more of sequence homology between a donor and a genomic sequence (or any integral value between 10 and 200 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology is present to support homologous recombination. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of the donor sequence, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV).

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homologous recombination. Applicants' methods advantageously combine the powerful targeting capabilities of engineered ZFPs with a cleavage domain (or cleavage half-domain) to specifically target a double-stranded break to the region of the genome at which recombination is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC3), genes whose products interact with the aforementioned gene products (e.g., BRCA1, BRCA2) and/or genes in the NBS1 complex. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Yanez et al. (1998) *Gene Therapy* 5:149-159; Hoeijmakers (2001) *Nature* 411:366-374; Johnson et al. (2001) *Biochem. Soc. Trans.* 29:196-201; Tauchi et al. (2002) *Oncogene* 21:8967-8980. Methods for activation and repression of gene expression using fusions between a zinc finger binding domain and a functional domain are disclosed in co-owned U.S. Pat. No. 6,534,261. Additional repression methods include the use of antisense oligonucleotides and/or small interfering RNA (siRNA or RNAi) targeted to the sequence of the gene to be repressed.

As an alternative to or, in addition to, activating expression of gene products involved in homologous recombination, fusions of these protein (or functional fragments thereof) with a zinc finger binding domain targeted to the region of interest, can be used to recruit these proteins (recombination proteins) to the region of interest, thereby increasing their local concentration and further stimulating homologous recombination processes. Alternatively, a polypeptide involved in homologous recombination as described above (or a functional fragment thereof) can be part of a triple fusion protein comprising a zinc finger binding domain, a cleavage domain (or cleavage half-domain) and the recombination protein (or functional fragment thereof). Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases.

The p53 protein has been reported to play a central role in repressing homologous recombination (HR). See, for example, Valerie et al., (2003) *Oncogene* 22:5792-5812; Janz, et al. (2002) *Oncogene* 21:5929-5933. For example, the rate of HR in p53-deficient human tumor lines is 10,000-fold greater than in primary human fibroblasts, and there is a 100-fold increase in HR in tumor cells with a non-functional p53 compared to those with functional p53. Mekeel et al. (1997) *Oncogene* 14:1847-1857. In addition, overexpression of p53 dominant negative mutants leads to a 20-fold increase in spontaneous recombination. Bertrand et al. (1997) *Oncogene* 14:1117-1122. Analysis of different p53 mutations has revealed that the roles of p53 in transcriptional transactivation and G1 cell cycle checkpoint control are separable from its involvement in HR. Saintigny et al. (1999) *Oncogene* 18:3553-3563; Boehden et al. (2003) *Oncogene* 22:4111-4117. Accordingly, downregulation of p53 activity can serve to increase the efficiency of targeted homologous recombination using the methods and compositions disclosed herein. Any method for downregulation of p53 activity can be used, including but not limited to cotransfection and overexpression of a p53 dominant negative mutant or targeted repression of p53 gene expression according to methods disclosed, e.g., in co-owned U.S. Pat. No. 6,534,261.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Methods to Screen for Cellular Factors that Facilitate Homologous Recombination

Since homologous recombination is a multi-step process requiring the modification of DNA ends and the recruitment of several cellular factors into a protein complex, the addition of one or more exogenous factors, along with donor DNA and vectors encoding zinc finger-cleavage domain fusions, can be used to facilitate targeted homologous recombination. An exemplary method for identifying such a factor or factors employs analyses of gene expression using microarrays (e.g., Affymetrix Gene Chip® arrays) to compare the mRNA expression patterns of different cells. For example, cells that exhibit a higher capacity to stimulate double strand break-driven homologous recombination in the presence of donor DNA and zinc finger-cleavage domain fusions, either unaided or under conditions known to increase the level of gene correction, can be analyzed for their gene expression patterns compared to cells that lack such capacity. Genes that are upregulated or downregulated in a manner that directly correlates with increased levels of homologous recombination are thereby identified and can be cloned into any one of a number of expression vectors. These expression constructs can be co-transfected along with zinc finger-cleavage domain fusions and donor constructs to yield improved methods for achieving high-efficiency homologous recombination. Alternatively, expression of such genes can be appropriately regulated using engineered zinc finger proteins which modulate expression (either activation or repression) of one or more these genes. See, e.g., co-owned U.S. Pat. No. 6,534,261 for methods for the synthesis of engineered zinc finger proteins for regulation of gene expression.

As an example, it was observed that the different clones obtained in the experiments described in Example 9 and FIG. 27 exhibited a wide-range of homologous recombination frequencies, when transfected with donor DNA and plasmids encoding zinc finger-cleavage domain fusions. Gene expression in clones showing a high frequency of targeted recombination can thus be compared to that in clones exhibiting a low frequency, and expression patterns unique to the former clones can be identified.

As an additional example, studies using cell cycle inhibitors (e.g., nocodazole or vinblastine, see e.g., Examples 11, 14 and 15) showed that cells arrested in the G2 phase of the cell cycle carried out homologous recombination at higher rates, indicating that cellular factors responsible for homologous recombination may be preferentially expressed or active in G2. One way to identify these factors is to compare the mRNA expression patterns between the stably transfected HEK 293 cell clones that carry out gene correction at high and low levels (e.g., clone T18 vs. clone T7). Similar comparisons are made between these cell lines in response to compounds that arrest the cells in G2 phase. Candidate genes that are differentially expressed in cells that carry out homologous recombination at a higher rate, either unaided or in response to compounds that arrest the cells in G2, are identified, cloned, and re-introduced into cells to determine whether their expression is sufficient to re-capitulate the improved rates. Alternatively, expression of said candidate genes is activated using engineered zinc finger transcription factors as described, for example, in co-owned U.S. Pat. No. 6,534,261.

Expression Vectors

A nucleic acid encoding one or more ZFPs or ZFP fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a ZFP can also be cloned into an expression vector, for administration to a plant cell, animal cell, preferably a mammalian cell or a human cell, fungal cell, bacterial cell, or protozoal cell.

To obtain expression of a cloned gene or nucleic acid, sequences encoding a ZFP or ZFP fusion protein are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., Gene 22:229-235 (1983)). Kits for such expression systems are commercially available. Eukaryotic expression systems for mammalian cells, yeast, and insect cells are well known by those of skill in the art and are also commercially available.

The promoter used to direct expression of a ZFP-encoding nucleic acid depends on the particular application. For example, a strong constitutive promoter is typically used for expression and purification of ZFP. In contrast, when a ZFP is administered in vivo for gene regulation, either a constitutive or an inducible promoter is used, depending on the particular use of the ZFP. In addition, a preferred promoter for administration of a ZFP can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). The MNDU3 promoter can also be used, and is preferentially active in CD34$^+$ hematopoietic stem cells.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the ZFP, e.g., expression in plants, animals, bacteria, fungus, protozoa, etc. (see expression vectors described below). Standard bacterial expression vectors include plasmids such as pBR322-based plasmids, pSKF, pET23D, and commercially available fusion expression systems such as GST and LacZ. An exemplary fusion protein is the maltose binding protein, "MBP." Such fusion proteins are used for purification of the ZFP. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMT010/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a ZFP encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acids Encoding Fusion Proteins and Delivery to Cells

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered ZFPs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Adeno-associated virus vectors include AAV serotypes 1, 2, 5, 6, 7, 8 and 9; as well as chimeric AAV serotypes, e.g., AAV 2/1 and AAV 2/5. Both single-stranded and double-stranded (e.g., self-complementary) AAV vectors can be used.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

DNA constructs may be introduced into the genome of a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227: 1229-1231). Generally, the *Agrobacterium* transformation system is used to engineer dicotyledonous plants (Bevan et al (1982) *Ann. Rev. Genet.* 16:357-384; Rogers et al (1986) *Methods Enzymol.* 118:627-641). The *Agrobacterium* transformation system may also be used to transform, as well as transfer, DNA to monocotyledonous plants and plant cells. See Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40.; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Delivery Vehicles

An important factor in the administration of polypeptide compounds, such as ZFP fusion proteins, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ZFPs across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Chem.* 270:1 4255-14258 (1995)).

Examples of peptide sequences which can be linked to a protein, for facilitating uptake of the protein into cells, include, but are not limited to: an 11 amino acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ZFPs. Membrane translocation domains (i.e., internalization domains) can also be selected from libraries of randomized peptide sequences. See, for example, Yeh et al. (2003) *Molecular Therapy* 7(5):S461, Abstract #1191.

Toxin molecules also have the ability to transport polypeptides across cell membranes. Often, such molecules (called "binary toxins") are composed of at least two parts: a translocation/binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Such peptide sequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker.

The ZFP can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a ZFP.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a ZFP) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a ZFP and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, *Biochim. Biophys. Acta* 443:629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858:161-168 (1986); Williams et al., *PNAS* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are known to those of skill in the art.

In certain embodiments, it is desirable to target liposomes using targeting moieties that are specific to a particular cell type, tissue, and the like. Targeting of liposomes using a variety of targeting moieties (e.g., ligands, receptors, and monoclonal antibodies) has been described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes of lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337-16342 (1990) and Leonetti et al., *PNAS* 87:2448-2451 (1990).

Dosages

For therapeutic applications, the dose administered to a patient, or to a cell which will be introduced into a patient, in the context of the present disclosure, should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the efficacy and $K_d$ of the particular ZFP employed, the nuclear volume of the target cell, and the condition of the patient, as well as the body weight or surface area of the patient to be treated. The size of the dose also will be determined by the existence, nature, and extent of any adverse side-effects that accompany the administration of a particular compound or vector in a particular patient.

The maximum therapeutically effective dosage of ZFP for approximately 99% binding to target sites is calculated to be in the range of less than about $1.5 \times 10^5$ to $1.5 \times 10^6$ copies of the specific ZFP molecule per cell. The number of ZFPs per cell for this level of binding is calculated as follows, using the volume of a HeLa cell nucleus (approximately 1000 μm³ or $10^{-12}$ L; *Cell Biology*, (Altman & Katz, eds. (1976)). As the HeLa nucleus is relatively large, this dosage number is recalculated as needed using the volume of the target cell nucleus. This calculation also does not take into account competition for ZFP binding by other sites. This calculation also assumes that essentially all of the ZFP is localized to the nucleus. A value of 100× $K_d$ is used to calculate approximately 99% binding of to the target site, and a value of 10× $K_d$ is used to calculate approximately 90% binding of to the target site. For this example, $K_d$=25 nM $$ZFP + \text{target site} \leftrightarrow \text{complex}$$

i.e., $DNA + \text{protein} \leftrightarrow DNA\text{: protein complex}$ $$K_d = \frac{[DNA][protein]}{[DNA\text{: protein complex}]}$$

When 50% of ZFP is bound, $$K_d = [protein]$$

So when [protein] = 25 nM and the nucleus volume is $10^{-12}$ L $$[protein] = (25 \times 10^{-9} \text{moles/L})(10^{-12} \text{L/nucleus})$$

$$(6 \times 10^{23} \text{molecules/mole})$$

$$= 15,000 \text{ molecules/nucleus for 50\% binding}$$

When 99% target is bound;

$$100 \times K_d = [protein]$$

$$100 \times K_d = [protein]$$

$$= 2.5 \ \mu M (2.5 \times 10^{-6} \text{moles/L})$$

$$(10^{-12} \text{L/nucleus})(6 \times 10^{23} \text{molecules/mole})$$

$$= \text{about } 1,500,000 \text{ molecules per nucleus}$$

for 99% binding of target site.

The appropriate dose of an expression vector encoding a ZFP can also be calculated by taking into account the average rate of ZFP expression from the promoter and the average rate of ZFP degradation in the cell. In certain embodiments, a weak promoter such as a wild-type or mutant HSV TK promoter is used, as described above. The dose of ZFP in micrograms is calculated by taking into account the molecular weight of the particular ZFP being employed.

In determining the effective amount of the ZFP to be administered in the treatment or prophylaxis of disease, the physician evaluates circulating plasma levels of the ZFP or nucleic acid encoding the ZFP, potential ZFP toxicities, progression of the disease, and the production of anti-ZFP antibodies. Administration can be accomplished via single or divided doses.

Pharmaceutical Compositions and Administration

ZFPs and expression vectors encoding ZFPs can be administered directly to the patient for targeted cleavage and/or recombination, and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by ZFP gene therapy include pathogenic bacteria, e.g., chlamydia, rickettsial bacteria, mycobacteria, staphylococci, streptococci, pneumococci, meningococci and conococci, *klebsiella, proteus, serratia, pseudomonas, legionella, diphtheria, salmonella*, bacilli, cholera, tetanus, botulism, anthrax, plague, leptospirosis, and Lyme disease bacteria; infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia*, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Applications

The disclosed methods and compositions for targeted cleavage can be used to induce mutations in a genomic sequence, e.g., large deletion mutations. Generation of targeted deletions, as disclosed herein, can be used to create gene knock-outs (e.g., for functional genomics or target validation) and for purposes of cell engineering or protein overexpression.

Targeted cleavage at a site in chromosomal DNA requires a pair of zinc finger/nuclease half-domain fusion proteins (ZFNs) so that dimerization of the cleavage half-domains occurs. Accordingly, for targeted deletion of long sequences, two pairs of ZFNs are used, to cleave at two sites and delete sequences between the two cleavage sites.

Targeted deletion of infecting or integrated viral genomes can be used to treat viral infections in a host. Additionally, targeted deletion of genes encoding receptors for viruses can be used to block expression of such receptors, thereby preventing viral infection and/or viral spread in a host organism. Targeted deletion of genes encoding viral receptors (e.g., the CCR5 and CXCR4 receptors for HIV) can be used to render the receptors unable to bind to virus, thereby preventing new infection and blocking the spread of existing infections. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M Knipe, eds. 1991), for a description of these and other viruses. Receptors for HIV, for example, include CCR-5 and CXCR-4.

In similar fashion, the genome of an infecting bacterium can be mutagenized by targeted deletion, to block or ameliorate bacterial infections.

Certain genetic diseases result from expression of a mutant gene product. In such cases, inactivation of the mutant gene product by targeted deletion of its gene may ameliorate or cure the disease. Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240), acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064. Treated stem cells can be returned to a patient for treatment of various diseases including, but not limited to, AIDS, SCID and sickle-cell anemia.

As another example, overexpression of an oncogene may be reversed either by mutating the gene or by inactivating its control sequences by deletion. Any pathology dependent upon expression of a particular genomic sequence can be corrected or alleviated by targeted deletion of part or all of the sequence.

Targeted deletion can also be used to alter non-coding sequences (e.g., regulatory sequences such as promoters, enhancers, initiators, terminators, splice sites) to alter the levels of expression of a gene product. Such methods can be used, for example, for therapeutic purposes, functional genomics and/or target validation studies.

The compositions and methods described herein also allow for novel approaches and systems to address immune reactions of a host to allogeneic grafts. In particular, a major problem faced when allogeneic stem cells (or any type of allogeneic cell) are grafted into a host recipient is the high risk of rejection by the host's immune system, primarily mediated through recognition of the Major Histocompatibility Complex (MHC) on the surface of the engrafted cells. The MHC comprises the HLA class I protein(s) that function as heterodimers that are comprised of a common β subunit and variable α subunits. It has been demonstrated that tissue grafts derived from stem cells that are devoid of HLA escape the host's immune response. See, e.g., Coffman et al. *J Immunol* 151, 425-35. (1993); Markmann et al. *Transplantation* 54, 1085-9. (1992); Koller et al. *Science* 248, 1227-30. (1990). Using the compositions and methods described herein, genes encoding HLA proteins involved in graft rejection can be mutagenized or altered by deletion, in either their coding or regulatory sequences, so that their expression is blocked or they express a non-functional product. For example, by inactivating the gene encoding the common β subunit gene (β2 microglobulin) using the methods and compositions described herein, HLA class I can be removed from the cells to rapidly and reliably generate HLA class I null stem cells from any donor, thereby reducing the need for closely matched donor/recipient MHC haplotypes during stem cell grafting.

Thus, inactivation of any gene (e.g., the β2 microglobulin gene, the CTLA4 gene) can be achieved, for example, by cleavage at two sites followed by joining so as to delete the sequence between the two cleavage sites.

Targeted modification of chromatin structure, as disclosed in co-owned WO 01/83793, can be used to facilitate the binding of fusion proteins to cellular chromatin.

EXAMPLES

The following examples show that targeted cleavage at two sites in chromosomal DNA can generate large deletions of genomic sequences, including deletion of sequences between the two cleavage sites. Targeted cleavage is accomplished, in certain embodiments, using fusion proteins (ZFNs) comprising a zinc finger DNA-binding domain and a nuclease half-domain.

Example 1: Design of Zinc Finger/Nuclease Half-Domain Fusion Proteins (ZFNs) Targeted to the Human CCR-5 Gene A number of zinc finger proteins were designed to bind to sites in the human CCR5 gene (GenBank® Accession Number AY221093). The proteins were designed in pairs such that, for each pair, target sites occurred on opposite DNA strands and the near edges of the target sites were separated by 5 nucleotide pairs.

Table 2 shows the nucleotide sequences of the target sites for these zinc finger domains, and the locations of the target sites within the human CCR-5 gene. The amino acid sequences of the recognition regions of their zinc finger portions are also shown.

Polynucleotides encoding fusions of the zinc finger domains shown in Table 2 to the Fold cleavage half-domain were constructed, in which sequences encoding the zinc finger domain are upstream of sequences encoding the cleavage half-domain, such that, in the encoded proteins, the zinc finger domain is nearest the N-terminus, and the cleavage half-domain is nearest the C-terminus, of the fusion protein.

TABLE 2

Zinc Finger Designs for the CCR-5 Gene[2]

| Name | Target sequence[1] | Location[3] | F1 | F2 | F3 | F4 |
|---|---|---|---|---|---|---|
| r162b2 | GATGAGGATGAC (SEQ ID NO: 2) | 151 to 162 | DRSNLSR (SEQ ID NO: 3) | TSANLSR (SEQ ID NO: 4) | RSDNLAR (SEQ ID NO: 5) | TSANLSR (SEQ ID NO: 4) |
| r162p11 | GATGAGGATGAC (SEQ ID NO: 2) | 151 to 162 | DRSNLSR (SEQ ID NO: 3) | VSSNLTS (SEQ ID NO: 6) | RSDNLAR (SEQ ID NO: 5) | TSANLSR (SEQ ID NO: 4) |
| 168c4 | AAACTGCAAAAG (SEQ ID NO: 7) | 168 to 179 | RSDHLSE (SEQ ID NO: 8) | QNANRIT (SEQ ID NO: 9) | RSDVLSE (SEQ ID NO: 10) | QRNHRTT (SEQ ID NO: 11) |
| 168i13 | AAACTGCAAAAG (SEQ ID NO: 7) | 168 to 179 | RSDNLSV (SEQ ID NO: 12) | QKINLQV (SEQ ID NO: 13) | RSDVLSE (SEQ ID NO: 10) | QRNHRTT (SEQ ID NO: 11) |
| r627s1 | GACAAGCAGCGG (SEQ ID NO: 14) | 616 to 627 | RSAHLSE (SEQ ID NO: 15) | RSANLSE (SEQ ID NO: 16) | RSANLSV (SEQ ID NO: 17) | DRANLSR (SEQ ID NO: 18) |
| 633a10 | CATCTGcTACTCG (SEQ ID NO: 19) | 633 to 645 | RSDSLSK (SEQ ID NO: 20) | DNSNRIK (SEQ ID NO: 21) | RSAVLSE (SEQ ID NO: 22) | TNSNRIT (SEQ ID NO: 23) |
| 633b5 | CATCTGctACTCGG (SEQ ID NO: 24) | 633 to 646 | RSDHLSE (SEQ ID NO: 8) | ARSTRTN (SEQ ID NO: 25) | RSAVLSE (SEQ ID NO: 22) | TNSNRIT (SEQ ID NO: 23) |

Notes:
[1]Nucleotides in uppercase represent those present in subsites bound by individual zinc fingers; those in lowercase represent nucleotides not present in a subsite
[2]The zinc finger amino acid sequences shown above (in one-letter code) represent residues −1 through +6, with respect to the start of the alpha-helical portion of each zinc finger. Finger F1 is closest to the amino terminus of the protein.
[3]Numbers in this column refer to nucleotide pairs downstream from the first residue of the translation initiation codon of the human CCR-5 gene Example 2: Targeted Deletion in the CCR5 Gene of $K_{562}$ Cells Using Two Pairs of Zinc Finger Nucleases K562 erythroleukemia cells were cultured in RPMI medium with 10% bovine serum. At a density of approximately $1 \times 10^6$ cells/ml, cells were transfected with two DNA constructs, each encoding a pair of zinc finger nucleases (ZFNs), with the ZFN coding sequences separated by a 2A peptide sequence. The first plasmid (denoted 004) encoded the r162b2 and 168c4 ZFNS (see Table 2 above) which were designed to cleave between +162 and +168 (with respect to the translation start) of the human CCR-5 gene; the second plasmid (denoted 043) encoded the r627s1 and 633b5 ZFNs (Table 2) which were designed to cleave between +627 and +633. Control transfections used only one of these two plasmids, or used a plasmid encoding green fluorescent protein (GFP).

Cells were concentrated 20-fold and transfection by nucleofection, using the AMAXA method (solution V and program T-16 for 2 million cells per 5 ug of each plasmid) following the manufacturer's protocol for K562 cells. Transfection efficiency was close to 90%, as estimated by expression of Green Fluorescent Protein as a control. Forty-eight hours after transfection, cells were harvested and genomic DNA was isolated using a Dneasy® Tissue kit (Qiagen, Valencia, Calif.), following the manufacturer's protocol. The genomic DNA (200-500 ng) was used as template for amplification using an AccuPrime® PCR amplification kit (Invitrogen, Carlsbad, Calif.) with the following primers:

```
                              (SEQ ID NO: 26)
CCR5longF:    GATGGTGCTTTCATGAATTCC
and
                              (SEQ ID NO: 27)
CCR5longR:    GTGTCACAAGCCCACAGATA.
```

Amplification products were analyzed by electrophoresis on 2% agarose e-gels (Invitrogen).

Figure 1:
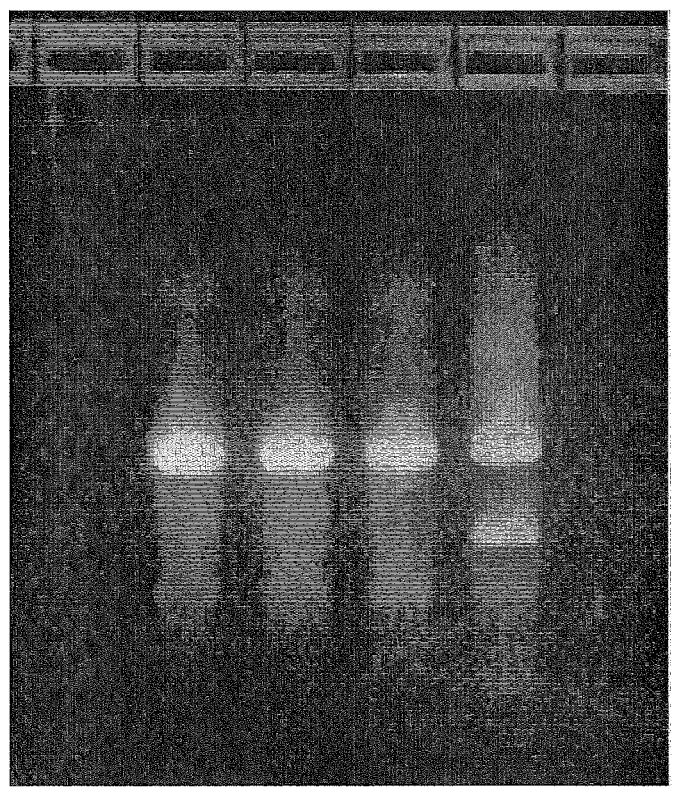
FIG. 1 is a photograph of an agarose gel in which amplification products of the human CCR-5 gene were analyzed. Lane 1 shows amplification products of DNA from K562 cells transfected with a plasmid encoding green fluorescent protein. Lane 2 shows amplification products of DNA from K562 cells transfected with a plasmid encoding a pair of ZFNs designed to cleave between +162 and +168 of the human CCR-5 gene. Lane 3 shows amplification products of DNA from K562 cells transfected with a plasmid encoding a pair of ZFNs designed to cleave between +627 and +633 of the human CCR-5 gene. Lane 4 shows amplification products of DNA from K562 cells transfected with both of the aforementioned ZFN pairs.

Results are shown in FIG. 1. In addition to a band corresponding to the amplification product obtained from chromosomes carrying a wild-type CCR-5 gene (present in all lanes), a lower molecular weight amplification product is obtained from cells transfected with plasmids encoding the two ZFN pairs (lane 4). The size of this low molecular-weight band is consistent with removal of approximately 465 nucleotide pairs from the CCR-5 sequences, which corresponds to the distance between the two targeted cleavage sites.

To confirm that targeted deletions of the endogenous CCR-5 gene had been obtained, amplification products were cloned into the Topo-4® vector (Invitrogen, Carlsbad, Calif.) following the manufacturer's protocol. Two classes of insert size were obtained. Plasmids containing inserts of the smaller size class were analyzed to determine the nucleotide sequence of their inserts. The results are shown in FIG. 2, in which a representative number of sequences in the region around and between the two targeted cleavage sites are shown. It can be seen, from the sequences obtained, that sequence alterations induced by cleavage at two cleavage sites can include deletion of some or all of the sequence between the two cleavage sites, and can also include deletion of additional sequences on one or both sides.

Analysis of genomic DNA by blotting was also conducted to provide an estimate of the frequency of deletion events resulting from targeted cleavage at two sites. Genomic DNA was isolated from K562 cells that had been transfected with plasmids encoding the two nuclease pairs described earlier in this example, or from control K562 cells that had been transfected with a plasmid encoding green fluorescent protein. Ten micrograms of DNA was digested with XhoI and NdeI. The digestion products were fractionated on an agarose gel and transferred to a nylon membrane. The membrane was incubated with a labeled probe comprising sequences corresponding to nucleotides −246 through +9, with respect to the first base pair of the translation initiation codon of the human CCR-5 gene.

The probe used in this experiment identifies a 2.8 kbp XhoI-NdeI fragment in DNA from cells transfected with the GFP-encoding plasmid, corresponding to wild-type CCR-5 sequences (FIG. 3, lane 2). In cells expressing the two ZFN pairs, however, a band at approximately 2.3 kbp, corresponding to deleted molecules, is also present (FIG. 3, lane 1). Quantitation of this lower molecular weight band indicated a deletion frequency of approximately 10%.

Example 3: Targeted Deletion in the CCR5 Gene of Human T-Cells Using Two Pairs of Zinc Finger Nucleases Human T-cells were obtained by leukopheresis from a healthy donor, the T cells were depleted in CD8 cells, then activated for two days with PHA+IL2. Transfection was performed by electroporation, using a Maxcyte electroporation device. Cells were transfected with two DNA constructs, each encoding a pair of zinc finger nucleases (ZFNs), with the ZFN coding sequences separated by a 2A peptide sequence. The first plasmid (denoted 149) encoded the r162 µl and 168i13 ZFNS (see Table 2 above) which were designed to cleave between +162 and +168 (with respect to the translation start) of the human CCR-5 gene; the second plasmid (denoted 141) encoded the r627s1 and 633a10 ZFNs (Table 2) which were designed to cleave between +627 and +633. Control transfections used a plasmid encoding green fluorescent protein (GFP).

5 million cells+20 ug of DNA (10 ug of each ZFN pair-encoding plasmid) were used per transfection. Transfected cells were collected by centrifugation 2 days after transfection. and genomic DNA was isolated using a DNeasy® Tissue kit (Qiagen, Valencia, Calif.), following the manufacturer's protocol. The genomic DNA (200-500 ng) was used as template for amplification using an AccuPrime® PCR amplification kit (Invitrogen, Carlsbad, Calif.) with the following primers:

```
                            (SEQ ID NO: 26)
CCR5longF:      GATGGTGCTTTCATGAATTCC
and (SEQ ID NO: 27)
CCR5longR:      GTGTCACAAGCCCACAGATA
```

Amplification products were analyzed by electrophoresis on 2% agarose e-gels (Invitrogen).

Results are shown in FIG. 4. In addition to a band corresponding to the amplification product obtained from chromosomes carrying a wild-type CCR-5 gene (lane 2 and 3 of FIG. 4), a lower molecular weight amplification product is obtained from cells transfected with plasmids encoding the two ZFN pairs (lane 2 of FIG. 4). The size of this low molecular-weight band is consistent with removal of approximately 465 nucleotide pairs from the CCR-5 sequences, which corresponds to the distance between the two targeted cleavage sites.

To confirm that targeted deletions of the endogenous CCR-5 gene had been obtained, the lower molecular weight band was excised from the gel, DNA was eluted from the band and cloned into the Topo-4® vector (Invitrogen, Carlsbad, Calif.) following the manufacturer's protocol. Resulting plasmids were analyzed to determine the nucleotide sequence of their inserts. The results are shown in FIG. 5, in which a representative number of sequences in the region around and between the two targeted cleavage sites are shown. It can be seen, from the sequences obtained, that the amplification products present in the lower band contained deletions of approximately 430 nucleotide pairs, whose endpoints lay at or near the targeted cleavage sites.

Example 4: Targeted Deletion in the CTLA4 Gene

A number of zinc finger proteins were designed to bind to sites in the human CTLA4 gene (GenBank® Accession Number NM_005214). The proteins were designed in pairs such that, for each pair, target sites occurred on opposite DNA strands. For one pair, the near edges of the target sites were separated by 5 nucleotide pairs and, for the other pair, the near edges of the target sites were separated by 6 nucleotide pairs.

Table 3 shows the nucleotide sequences of the target sites for these zinc finger domains, and the locations of the target sites within the human CTLA4 gene. The amino acid sequences of the recognition regions of their zinc finger portions are also shown.

Polynucleotides encoding fusions of the zinc finger domains shown in Table 3 to the FokI cleavage half-domain were constructed, in which sequences encoding the zinc finger domain are upstream of sequences encoding the cleavage half-domain, such that, in the encoded proteins, the zinc finger domain is nearest the N-terminus, and the cleavage half-domain is nearest the C-terminus, of the fusion protein.

TABLE 3

Zinc Finger Designs for the CTLA4 Gene[2]

| Name | Target sequence[1] | Location[3] | F1 | F2 | F3 | F4 |
|---|---|---|---|---|---|---|
| r158a | ATGGCTTTATGG (SEQ ID NO: 28) | 147 to 158 | RSDHLSQ (SEQ ID NO: 29) | TSSARTN (SEQ ID NO: 30) | QSSDLSR (SEQ ID NO: 31) | RSDALTQ (SEQ ID NO: 32) |
| 164a | GCCTTGGATTTC (SEQ ID NO: 33) | 164 TO 175 | TNLPLNN (SEQ ID NO: 34) | TSSNLSR (SEQ ID NO: 35) | RSDSLSA (SEQ ID NO: 36) | DRSDLSR (SEQ ID NO: 37) |
| r2902b | ACCCGGaCCTCAG (SEQ ID NO: 38) | 2890 to 2902 | RSDHLSE (SEQ ID NO: 8) | TSSTRKT (SEQ ID NO: 39) | RSDHLSE (SEQ ID NO: 8) | TSSDRTK (SEQ ID NO: 40) |
| 2909b | GCTTCGgCAGGCT (SEQ ID NO: 41) | 2909 to 2921 | QSSDLSR (SEQ ID NO: 31) | RSDNLRE (SEQ ID NO: 42) | RSDDLSK (SEQ ID NO: 43) | QSSDLRR (SEQ ID NO: 44) |

Notes:
[1]Nucleotides in uppercase represent those present in subsites bound by individual zinc fingers; those in lowercase represent nucleotides not present in a subsite
[2]The zinc finger amino acid sequences shown above (in one-letter code) represent residues -1 through +6, with respect to the start of the alpha-helical portion of each zinc finger. Finger F1 is closest to the amino terminus of the protein.
[3]Numbers in this column refer to nucleotide pairs downstream from the first residue of the translation initiation codon of the human CTLA4 gene K562 cells were cultured and transfected as described in Example 2. Cells were transfected with four DNA constructs, each encoding one of the zinc finger nucleases (ZFNs) identified in Table 3. Control transfections were conducted with a vector that did not encode a ZFN ("empty vector").

Transfected cells were collected by centrifugation 2 days after transfection. and genomic DNA was isolated using a DNeasy® Tissue kit (Qiagen, Valencia, Calif.), following the manufacturer's protocol. Genomic DNA (200 ng) was used as template for amplification using an AccuPrime® PCR amplification kit (Invitrogen, Carlsbad, Calif.) with primers that yield a 3.8 kilobase pair (kbp) amplification product from a wild-type CTLA4 gene. Amplification products were analyzed by gel electrophoresis.

The results indicated that, in addition to a band corresponding to the 3.8 kbp amplification product obtained from chromosomes carrying a wild-type CTLA4 gene, a lower molecular weight amplification product of approximately 1 kbp was obtained from cells that were transfected with plasmids encoding the four ZFNs. The size of this low molecular-weight band is consistent with removal of approximately 2.8 kilobase pairs from the CTLA4 locus, which corresponds to the distance between the two targeted cleavage sites.

Nucleotide sequence analysis of amplification products, similar to that described in Example 3, confirmed that the endpoints of the deletions lay at or near the targeted cleavage sites in the endogenous CTLA4 gene.

Similar results were obtained using a second pair of ZFNs designed to cleave between +3104 and +3111, in combination with the r158a and 164a nucleases described in Table 3.

Similar results were also obtained in primary human T-cells (obtained from AllCells Berkeley, Calif.) using both combinations of ZFN pairs.

Example 5: Targeted Deletion of the Human IL-2Rγ Gene

Two pairs of zinc finger/nuclease half-domain fusion proteins, designed to cleave in the third exon of the IL-2Rγ ("common gamma chain") gene have been disclosed in parent application Publication No. 2005-0064474, the disclosure of which is incorporated by reference (See Example 2 of that application). Two pairs of zinc finger/nuclease half-domain fusion proteins designed to cleave in the fifth exon of the IL-2Rγ gene are also disclosed in that application (See Examples 5 and 14 of U.S. patent application Publication No. 2005-0064474, incorporated by reference).

Co-expression in cells of either of the first pair of exon 3-targeted nucleases and either of the second pair of exon 5-targeted nucleases (e.g., by transfection of cells with plasmids encoding the nucleases), using methods similar to those described in the previous examples, results, in cleavage events in exon 3 and exon 5 of the IL-2Rγ gene. Subsequent rejoining of DNA ends can result in loss of sequences between the cleavage sites, leading to deletion of approximately 1,400 nucleotide pairs of the X chromosome.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for deleting at least 100 nucleotide pairs in a region of interest in endogenous double-stranded DNA in a plant or mammalian cell, the method comprising:
   expressing first, second, third and fourth fusion proteins in the cell, each of the fusion proteins comprising:
   (i) a zinc finger DNA-binding domain that binds to a target site in the endogenous DNA, and
   (ii) a cleavage half-domain;
   further wherein:
   (a) the first and second fusion proteins bind to first and second target sites respectively, wherein a first cleavage site lies between the first and second target sites, wherein the first and second target sites, each target site comprising at least 3 target subsites, and
   (b) the third and fourth fusion proteins bind to third and fourth target sites respectively, wherein a second cleavage site lies between the third and fourth target sites and wherein the first and second cleavage sites are within different sequences;
   such that the first and second fusion proteins cleave the DNA at the first cleavage site, the third and fourth fusion proteins cleave the DNA at the second cleavage site, and DNA ends are rejoined such that at least 100 endogenous nucleotide pairs between the first and second cleavage sites are deleted and at least two of the target sites are maintained in the endogenous double-stranded DNA following deletion of the at least 100 endogenous nucleotide pairs.

2. The method of claim 1, wherein the first and second cleavage sites are on the same chromosome.

3. The method of claim 1, wherein the near edges of the first and second target sites are separated by between 4 and 6 nucleotide pairs.

4. The method of claim 1, wherein the near edges of the third and fourth target sites are separated by between 4 and 6 nucleotide pairs.

5. The method of claim 1, wherein at least 400 nucleotide pairs between the first and second cleavage sites are deleted.

6. The method of claim 5, wherein at least 1000 nucleotide pairs between the first and second cleavage sites are deleted.

7. The method of claim 1, wherein the cell is a primary cell.

8. The method of claim 7, wherein the cell is a T-cell.

9. The method of claim 1, wherein the first and second cleavage sites are separated by more than 100 nucleotide pairs.

10. The method of claim 1, wherein the target site is in a CCR5 gene, β2 microglobulin gene or CTLA4 gene.

* * * * *